United States Patent
Dugar et al.

(10) Patent No.: US 11,083,720 B2
(45) Date of Patent: Aug. 10, 2021

(54) INDAZOLE INHIBITORS OF FRUCTOKINASE (KHK) AND METHODS OF USE IN TREATING KHK-MEDIATED DISORDERS OR DISEASES

(71) Applicant: REGENTS OF THE UNIVERSITY OF COLORADO, A BODY CORPORATE, Denver, CO (US)

(72) Inventors: Sundeep Dugar, San Jose, CA (US); Miguel Lanaspa-Garcia, Denver, CO (US); MyPhuong Thi Le, Denver, CO (US); William John Greenlee, Teaneck, NJ (US)

(73) Assignees: Regents of the University of Colorado, a body corporate, Denver, CO (US); Colorado Research Partners. LLC, Centennial, CO (US)

( * ) Notice: Subject to any disclaimer, the term of this patent is extended or adjusted under 35 U.S.C. 154(b) by 0 days.

(21) Appl. No.: 16/494,946

(22) PCT Filed: Mar. 19, 2018

(86) PCT No.: PCT/US2018/023186
§ 371 (c)(1),
(2) Date: Sep. 17, 2019

(87) PCT Pub. No.: WO2018/170517
PCT Pub. Date: Sep. 20, 2018

(65) Prior Publication Data
US 2020/0016141 A1 Jan. 16, 2020

Related U.S. Application Data

(60) Provisional application No. 62/473,005, filed on Mar. 17, 2017.

(51) Int. Cl.
| | | |
|---|---|---|
| *A61K 31/4439* | (2006.01) | |
| *A61P 3/08* | (2006.01) | |
| *A61K 31/416* | (2006.01) | |
| *A61K 31/496* | (2006.01) | |
| *C07D 401/10* | (2006.01) | |
| *C07D 401/12* | (2006.01) | |
| *C07D 401/14* | (2006.01) | |
| *C07D 403/12* | (2006.01) | |

(52) U.S. Cl.
CPC ........ *A61K 31/4439* (2013.01); *A61K 31/416* (2013.01); *A61K 31/496* (2013.01); *A61P 3/08* (2018.01); *C07D 401/10* (2013.01); *C07D 401/12* (2013.01); *C07D 401/14* (2013.01); *C07D 403/12* (2013.01)

(58) Field of Classification Search
None
See application file for complete search history.

(56) References Cited

U.S. PATENT DOCUMENTS

| | | |
|---|---|---|
| 6,294,538 B1 | 9/2001 | Mylari |
| 6,570,013 B2 | 5/2003 | Mylari |
| 6,894,047 B2 | 5/2005 | Mylari |
| 2005/0020578 A1 | 1/2005 | Chu-Moyer et al. |
| 2011/0263559 A1 | 10/2011 | Zhang et al. |

FOREIGN PATENT DOCUMENTS

| | | |
|---|---|---|
| WO | 2008057856 A2 | 5/2008 |
| WO | 2010082044 A1 | 7/2010 |
| WO | 2011133750 A1 | 10/2011 |
| WO | 2016109501 A1 | 7/2016 |

OTHER PUBLICATIONS

Database Registry Chemical Abstracts Service, Columbus, Ohio, Accession No. RN 1242430-71-2, Entered STN: Sep. 23, 2010.*
PCT/US2018/023186; International Search Report and Written Opinion; dated Aug. 23, 2018, 15 pages.
EP18766696.1; Extended European Search Report; dated Oct. 13, 2020; 7 pages.
Zhang Xuqing et al., "Optimization of a pyrazole hit from FBDD into a novel series of indazoles as ketohexokinase inhibitors", Bioorganic & Medicinal Chemistry Letters, 2011, vol. 21, pp. 4762-4767.

* cited by examiner

*Primary Examiner* — Samantha L Shterengarts
(74) *Attorney, Agent, or Firm* — Timothy H. Van Dyke; Wolter Van Dyke Davis, PLLC

(57) ABSTRACT

Disclosed herein are novel indazole-based compounds that inhibit fructokinase (aka ketohexokinase) and the downstream metabolic effects mediated by fructose metabolism. Fructokinase inhibitors specifically block the metabolism of both dietary and endogenous fructose metabolism and have a host of potential metabolic benefits. These benefits including blocking sugar craving and sugar induced metabolic syndrome and diabetes, but also blocking fructose metabolism can benefit the rare orphan disease Hereditary Fructose Intolerance, obesity, insulin resistance, metabolic syndrome, fatty liver, hypertension, cardiac injury from ischemia, certain cancers (including hepatocellular and pancreas), acute kidney injury from ischemia, heat stress, rhabdomyolysis or radiocontrast, and chronic diabetic and nondiabetic renal disease.

13 Claims, 1 Drawing Sheet

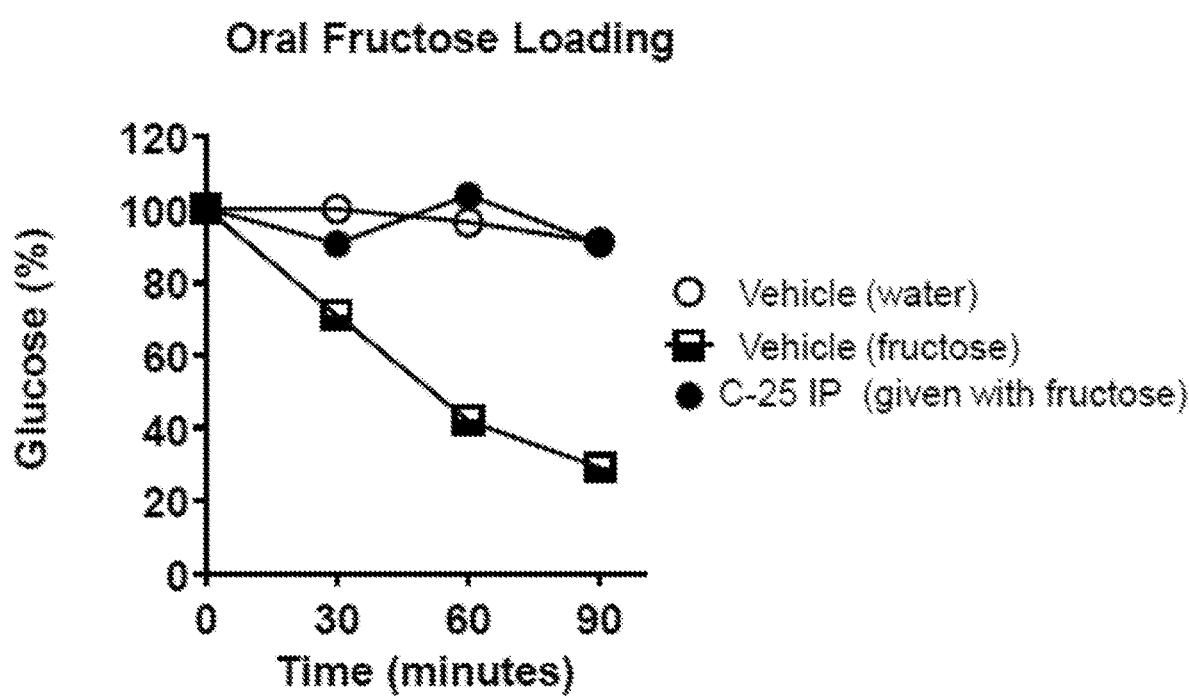

INDAZOLE INHIBITORS OF FRUCTOKINASE (KHK) AND METHODS OF USE IN TREATING KHK-MEDIATED DISORDERS OR DISEASES

FEDERAL FUNDING

This application was made with government support under an STTR Phase I awarded by the National Institutes of Health (NIH R41 DK104432-01). The government may have certain rights in the application.

FIELD OF INVENTION

This disclosure relates generally to indazole-based compounds and more specifically to indazole-based compounds that inhibit fructokinase (aka ketohexokinase) and the downstream metabolic effects mediated by fructose metabolism.

BACKGROUND

Fructokinase (ketohexokinase, KHK) is a key enzyme in fructose metabolism, and phosphorylates fructose to fructose-1-phosphate. In turn, fructose 1-phosphate is metabolized by aldolase B and triokinase to dihydroxyacetone phosphate and glyceraldehyde 3-phosphate, which leads eventually to glycolysis and the generation of triglycerides. There are two isoforms of fructokinase, fructokinase C and fructokinase A. Fructokinase C is a rapid phosphorylator, and causes a transient fall in intracellular ATP and phosphate during the metabolism of fructose[1].

Studies show that it is the fructokinase C isoform that is responsible for how fructose induces the metabolic syndrome, fatty liver, and cardiovascular and renal disease[1,2]. Blocking fructokinase also protects against sugar craving and sugar-induced hunger and impaired satiety from leptin resistance. In contrast, fructokinase A may have a role in hepatic carcinoma.[3] While much of human exposure to fructose comes from dietary sources of fructose, such as table sugar (sucrose), high fructose corn syrup (HFCS), honey and fruits, fructose can also be generated endogenously from glucose via the aldose reductase pathway and may play an important role in the mechanism by which high glycemic carbohydrates and salt induce metabolic syndrome and fatty liver, how heat stress and dehydration causes kidney disease, and also how diabetes mediates some of its complications, including renal disease and fatty liver.[4-6] Hereditary Fructose Intolerance (HFI) is a rare hereditary disease caused by aldolase B deficiency, the enzyme that metabolizes fructose-1-phosphate (the enzymatic step after fructokinase). The disease is characterized by rapid clinical symptoms in response to fructose ingestion, including hypoglycemia and lactate generation, with long-term manifestations including chronic liver disease. Fructokinase inhibition will also block the clinical manifestations of HFI in response to fructose.

Since the effects of fructose ingestion and metabolism are implicated in numerous diseases, there is a need for new fructokinase inhibitors. Such inhibitors may be important in treating multiple fructose mediated disorders.

BRIEF SUMMARY

Various embodiments relate to indazole-based compounds that inhibit fructokinase (aka ketohexokinase) and the downstream metabolic effects mediated by fructose metabolism. Various embodiments provide fructokinase inhibitors that specifically block both the metabolism of both dietary and endogenous fructose metabolism and have a host of potential metabolic benefits. These benefits may include blocking sugar craving and sugar induced metabolic syndrome and diabetes. Additionally, blocking fructose metabolism can benefit the rare orphan disease Hereditary Fructose Intolerance, obesity, insulin resistance, metabolic syndrome, fatty liver, hypertension, cardiac injury from ischemia, certain cancers (including hepatocellular and pancreas), acute kidney injury from ischemia, heat stress, rhabdomyolysis or radiocontrast, and chronic diabetic and nondiabetic renal disease.

BRIEF DESCRIPTION OF THE DRAWINGS

FIG. 1 presents a graph showing the results on glucose levels vs. vehicle (water) or vehicle (fructose) upon administration of compound C-25 described herein.

DETAILED DESCRIPTION

Exemplary Therapeutic Agents

Various embodiments relate to fructokinase inhibitor compounds as set forth in Formula I below:

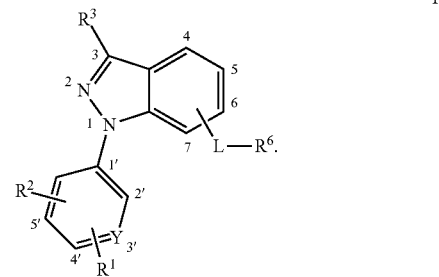

I

Referring to Formula I, $R^1$, $R^2$ may be independently selected from: —H, D, —$C_1$-$C_5$-straight chain alkyl, —$C_1$-$C_5$-branched alkyl, —$C_3$-$C_5$-cycloalkyl, —$(CH_2)_n$—$C_3$-$C_5$-cycloalkyl, —NH—$(CH_2)_n$—$C_3$-$C_5$-cycloalkyl —F, —Cl, —Br, —$CF_3$, —$CHF_2$, —$OCF_3$, —$OCHF_2$, —O—$C_3$-$C_5$-cycloalkyl, —O—$C_3$-$C_5$-alkyl, —CN, —$SO_2$—$C_1$-$C_4$-alkyl, —$SO_2CF_3$, —$SO_2$—$C_1$-$C_4$-cycloalkyl, —$Si(CH_3)_3$, —C≡C—$C_1$-$C_4$-alkyl, —C≡C—$C_3$-$C_5$-cycloalkyl; $COOR^5$, $CON(R^5)_2$, and $SO_2N(R^5)_2$, wherein n may be from 1-4.

Still referring to Formula I, $R^3$ may be selected from: —H, -cyclopropyl, -cyclobutyl, —$CH_2OCH_3$, 3-oxetanyl, —O—$C_3$-$C_5$-cycloalkyl, —$C(R^5)_2O$—$C_1$-$C_4$-alkyl, and —$CH_2O$—$C_3$-$C_5$-cycloalkyl.

Still referring to Formula I, L may represent simply a covalent bond to an $R^6$ group, as described below, or to a moiety selected from: —O—, —$NR^5$—, —$CONR^5$—, —$NR^5CO$—, —O—$[C(R^5)_2]_n$—, —$CH_2OCH_2$—, —[C$(R^5)_2]_n$—O—, —CO—, —$[C(R^5)_2]_n$—, —$CR^5(OH)$—, —$[C(R^5)_2]_n$—$NR^5$—, —$SO_2N(R^5)$—, —$SO_2$—, and —N—$[C(R^5)_2]_n$, wherein n may be from 1-4. $R^5$ may be selected independently from: —H, and a $C_1$-$C_5$-alkyl.

Still referring to Formula I, $R^6$ may be selected from: —$(CH_2)_n$—$N(R^5)_2$, 2-pyridyl, 3-pyridyl, 4-pyridyl, 3-pyridazinyl, 4-pyridazinyl, 1-piperazinyl, pyrimidin-2-yl, pyrimidin-4-yl, pyrimidin-5-yl, 4-piperidinyl, 3-piperidinyl, 3-azetidinyl, 3-pyrolidinyl, 4-imidazolyl, 4-imidazolyl, 1,2, 4-oxadiazol-5-yl, 1,2,4-triazol-3-yl, benzimidazol-5-yl, indol-5-yl, each of which may be substituted with from 1 to 3 R[4] substituents, which may be selected from $C_1$-$C_5$-alkyl, $C_3$-$C_7$-cycloalkyl, —N(R[5])2, —Cl, —F, —Br, —OR[5], —O—$C_3$-$C_7$-cycloalkyl, —CN, —$CF_3$, —$CHF_2$, —$OCF_3$, —$OCHF_2$, except where such substitution would be expected to yield unstable compounds. n may be from 1-4.

Still referring to Formula I, when L is selected from —CO, —O($CH_2$)$_2$—, —($CH_2$)$_n$, R[6] may be selected from: 2-azaspiro[3.3]heptan-6-yl, octahydropyrrolo[3,4-c]pyrrol-1-yl, 1-piperazinyl, 2,6-diazaspiro[3.3]heptan-1-yl,

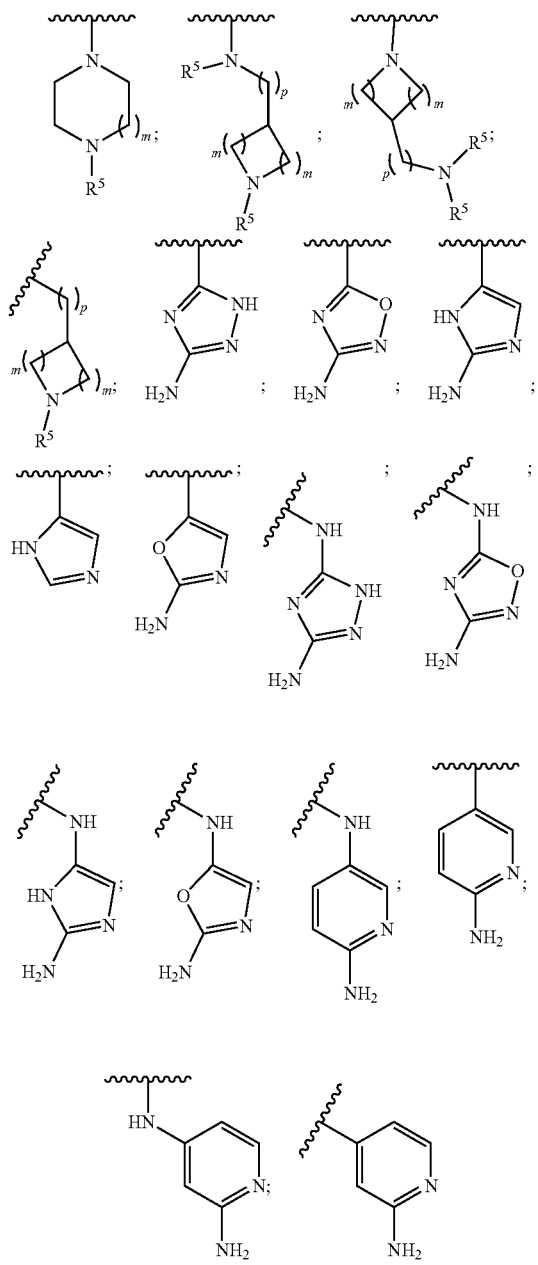

m = 1,2
p = 0, 1, 2, 3

Finally, still referring to Formula I, Y may be selected from N and CH.

Further embodiments relate to compounds as set forth in Formula II below:

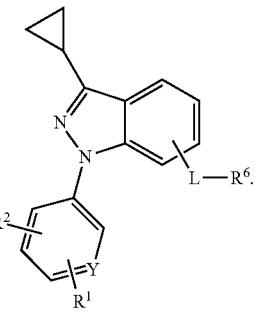

II

As shown in Formula II, R[1] may be selected from: —H, —$C_1$-$C_5$-alkyl, —$C_3$-$C_5$-cycloalkyl, —($CH_2$)$_n$—$C_3$-$C_5$-cycloalkyl, —F, —Cl, —Br, —$CF_3$, —$CHF_2$, —$OCF_3$, —$OCHF_2$, —O—$C_3$-$C_5$-cycloalkyl, —CN, —$SO_2$—$C_1$-$C_4$-alkyl, —$SO_2CF_3$, —$SO_2$—$C_1$-$C_4$-cycloalkyl, —Si($CH_3$)$_3$, —C≡C—$C_1$-$C_4$-alkyl, and —C≡C—$C_3$-$C_5$-cycloalkyl, wherein n may be from 1 to 4.

Still referring to Formula II, R[2] may be selected from: —H, —$C_1$-$C_5$-alkyl, —$C_3$-$C_5$-cycloalkyl, —($CH_2$)$_n$—$C_3$-$C_5$-cycloalkyl, —F, —Cl, —Br, —$CF_3$, —$CHF_2$, —$OCF_3$, —$OCHF_2$, —O—$C_3$-$C_5$-cycloalkyl, —CN, —$SO_2$—$C_1$-$C_4$-alkyl, —$SO_2CF_3$, —$SO_2$—$C_1$-$C_4$-cycloalkyl, —Si($CH_3$)$_3$, —C≡C—$C_1$-$C_4$-alkyl, and —C≡C—$C_3$-$C_5$-cycloalkyl, wherein n may be from 1 to 4.

Still referring to Formula II, L may represent simply a covalent bond to an R[6] group, as described below, or to a moiety selected from: —O—, —CONR[5]—, O—CH(R[5])—, —$CH_2OCH_2$—, —CH(R[5])—O—, —O($CH_2$) 2-, —CO—, —($CH_2$)$_n$—, and —CH(OH)—, wherein R[5] may be selected from: —H, and $C_1$-$C_5$-alkyl, and, wherein n may be from 1 to 4.

Still referring to Formula II, R[6] may be selected from: —($CH_2$)$_n$—N(R[5])$_2$, 2-pyridyl, 3-pyridyl, 4-pyridyl, 3-pyridazinyl, 4-pyridazinyl, 1-piperazinyl, pyrimidin-2-yl, pyrimidin-4-yl, pyrimidin-5-yl, 4-piperidinyl, 3-piperidinyl, 3-azetidinyl, 3-pyrolidinyl, 3-imidazolyl, 4-imidazolyl, 1,2,4-oxadiazol-5-yl, 1,2,4-triazol-3-yl, benzimidazol-5-yl, and indol-5-yl, each of which may be substituted with from 1 to 3 R[4] substituents, which may be selected from: $C_1$-$C_5$-alkyl, $C_1$-$C_5$-cycloalkyl, —N(R[5])$_2$, —Cl, —F, —Br, —OR[5], —O— cyclopropyl, —CN, —$CF_3$, —$CHF_2$, —$OCF_3$, and —$OCHF_2$, except where such substitution would be expected to yield unstable compounds. n may be from 1-4.

Still referring to Formula II, when L is selected from —CO, —O($CH_2$)$_2$—, and —($CH_2$)$_n$, R[6] may be selected from: 2-azaspiro[3.3]heptan-6-yl, octahydropyrrolo[3,4-c]pyrrol-1-yl, 1-piperazinyl, 2,6-diazaspiro[3.3]heptan-1-yl,

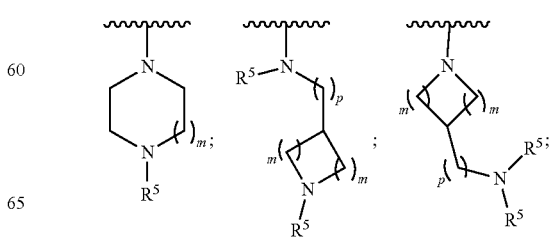

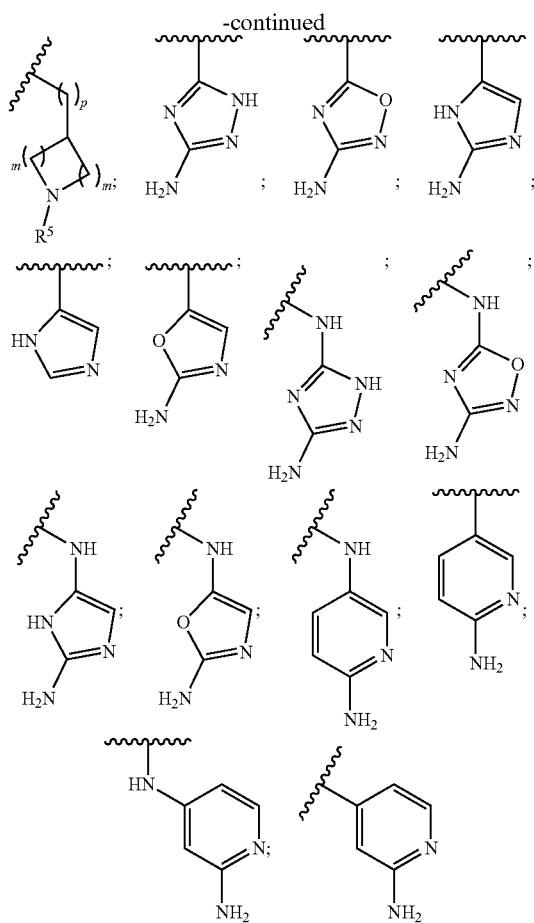

m = 1,2
p = 0, 1, 2, 3

Finally, still referring to Formula II, Y may be selected from N and CH.

Other embodiments pertain to compounds set forth in Formula III below:

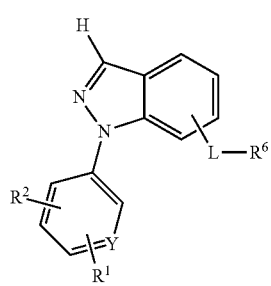

III

As shown in Formula III, $R^1$ may be selected from: —H, —$C_1$-$C_5$-alkyl, —$C_3$-$C_5$-cycloalkyl, —$(CH_2)_n$—$C_3$-$C_5$-cycloalkyl, —F, —Cl, —Br, —$CF_3$, —$CHF_2$, —$OCF_3$, —$OCHF_2$, —O—$C_3$-$C_5$-cycloalkyl, —CN, —$SO_2$—$C_1$-$C_4$-alkyl, —$SO_2CF_3$, —$SO_2$—$C_1$-$C_4$-cycloalkyl, —$Si(CH_3)_3$, —C≡C—$C_1$-$C_4$-alkyl, and —C≡C—$C_3$-$C_5$-cycloalkyl, wherein n may be from 1 to 4.

Still referring to Formula III, $R^2$ may be selected from: —H, —$C_1$-$C_5$-alkyl, —$C_3$-$C_5$-cycloalkyl, —$(CH_2)_n$—$C_3$-$C_5$-cycloalkyl, —F, —Cl, —Br, —$CF_3$, —$CHF_2$, —$OCF_3$, —$OCHF_2$, —O—$C_3$-$C_5$-cycloalkyl, —CN, —$SO_2$—$C_1$-$C_4$-alkyl, —$SO_2CF_3$, —$SO_2$—$C_1$-$C_4$-cycloalkyl, —$Si(CH_3)_3$, —C≡C—$C_1$-$C_4$-alkyl, and —C≡C—$C_3$-$C_5$-cycloalkyl, wherein n may be from 1 to 4.

Still referring to Formula III, L may represent simply a covalent bond to an $R^6$ group, as described below, or to a moiety selected from: —O—, —$CONR^5$—, O—$CH(R^5)$—, —$CH_2OCH_2$—, —$CH(R^5)$—O—, —$O(CH_2)_2$—, —CO—, —$(CH_2)_n$—, and —CH(OH)—, wherein $R^5$ may be selected from: —H, and $C_1$-$C_5$-alkyl, and, wherein n may be from 1 to 4.

Still referring to Formula III, $R^6$ may be selected from: —$(CH_2)_n$—$N(R^5)_2$, 2-pyridyl, 3-pyridyl, 4-pyridyl, 3-pyridazinyl, 4-pyridazinyl, 1-piperazinyl, pyrimidin-2-yl, pyrimidin-4-yl, pyrimidin-5-yl, 4-piperidinyl, 3-piperidinyl, 3-azetidinyl, 3-pyrolidinyl, 3-imidazolyl, 4-imidazolyl, 1,2,4-oxadiazol-5-yl, 1,2,4-triazol-3-yl, benzimidazol-5-yl, indol-5-yl, each of which may be substituted with one to three $R^4$ substituents, which may be selected from: $C_1$-$C_5$-alkyl, $C_1$-$C_5$-cycloalkyl, —$N(R^5)_2$, —Cl, —F, —Br, —$OR^5$, —O— cyclopropyl, —CN, —$CF_3$, —$CHF_2$, —$OCF_3$, and —$OCHF_2$, except where such substitution would be expected to yield unstable compounds. n may be from 1-4.

Still referring to Formula III, when L is selected from —CO, —$O(CH_2)_2$—, and —$(CH_2)_n$, $R^6$ may be selected from: 2-azaspiro[3.3]heptan-6-yl, octahydropyrrolo[3,4-c]pyrrol-1-yl, 1-piperazinyl, 2,6-diazaspiro[3.3]heptan-1-yl,

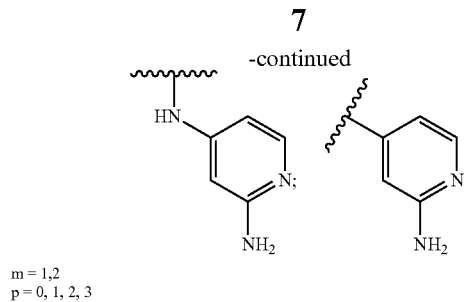

m = 1,2
p = 0, 1, 2, 3

Finally, still referring to Formula III, Y may be selected from N and CH.

Various embodiments pertain to compounds as set forth in Formula IV below:

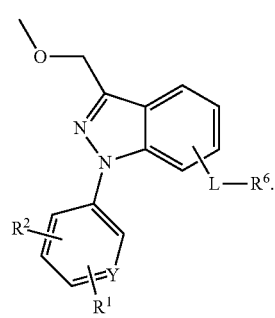

IV

Referring to Formula IV, $R^1$ may be selected from: —H, —$C_1$-$C_5$-alkyl, —$C_3$-$C_5$-cycloalkyl, —$(CH_2)_n$—$C_3$-$C_5$-cycloalkyl, —F, —Cl, —Br, —$CF_3$, —$CHF_2$, —$OCF_3$, —$OCHF_2$, —O—$C_3$-$C_5$-cycloalkyl, —CN, —$SO_2$—$C_1$-$C_4$-alkyl, —$SO_2CF_3$, —$SO_2$—$C_1$-$C_4$-cycloalkyl, —Si$(CH_3)_3$, —C≡C—$C_1$-$C_4$-alkyl, and —C≡C—$C_3$-$C_5$-cycloalkyl, wherein n may be from 1 to 4.

Still referring to Formula IV, $R^2$ may be selected from: —H, —$C_1$-$C_5$-alkyl, —$C_3$-$C_5$-cycloalkyl, —$(CH_2)_n$—$C_3$-$C_5$-cycloalkyl, —F, —Cl, —Br, —$CF_3$, —$CHF_2$, —$OCF_3$, —$OCHF_2$, —O—$C_3$-$C_5$-cycloalkyl, —CN, —$SO_2$—$C_1$-$C_4$-alkyl, —$SO_2CF_3$, —$SO_2$—$C_1$-$C_4$-cycloalkyl, —Si$(CH_3)_3$, —C≡C—$C_1$-$C_4$-alkyl, and —C≡C—$C_3$-$C_5$-cycloalkyl, wherein n may be from 1 to 4.

Still referring to Formula IV, L may represent simply a covalent bond to an $R^6$ group, as described below, or to a moiety selected from: —O—, —$CONR^5$—, O—$CH(R^5)$—, —$CH_2OCH_2$—, —$CH(R^5)$—O—, —$O(CH_2)$ 2-, —CO—, —$(CH_2)_n$—, and —CH(OH)—, wherein $R^5$ may be selected from: —H, and $C_1$-$C_5$-alkyl, and, wherein n may be from 1 to 4.

Still referring to Formula IV, $R^6$ may be selected from: —$(CH_2)_n$—$N(R^5)_2$, 2-pyridyl, 3-pyridyl, 4-pyridyl, 3-pyridazinyl, 4-pyridazinyl, 1-piperazinyl, pyrimidin-2-yl, pyrimidin-4-yl, pyrimidin-5-yl, 4-piperidinyl, 3-piperidinyl, 3-azetidinyl, 3-pyrolidinyl, 3-imidazolyl, 4-imidazolyl, 1,2,4-oxadiazol-5-yl, 1,2,4-triazol-3-yl, benzimidazol-5-yl, and indol-5-yl, each of which may be substituted with one to three $R^4$ substituents, which may be selected from: $C_1$-$C_5$-alkyl, $C_1$-$C_5$-cycloalkyl, —$N(R^5)$ 2, —Cl, —F, —Br, —$OR^5$, —O-cyclopropyl, —CN, —$CF_3$, —$CHF_2$, —$OCF_3$, and —$OCHF_2$, except where such substitution would be expected to yield unstable compounds. n may be from 1-4.

Still referring to Formula IV, when L is selected from —CO—, —$O(CH_2)_2$—, and —$(CH_2)_n$—, $R^6$ may be selected from: 2-azaspiro[3.3]heptan-6-yl, octahydropyrrolo[3,4-c]pyrrol-1-yl, 1-piperazinyl, 2,6-diazaspiro[3.3]heptan-1-yl,

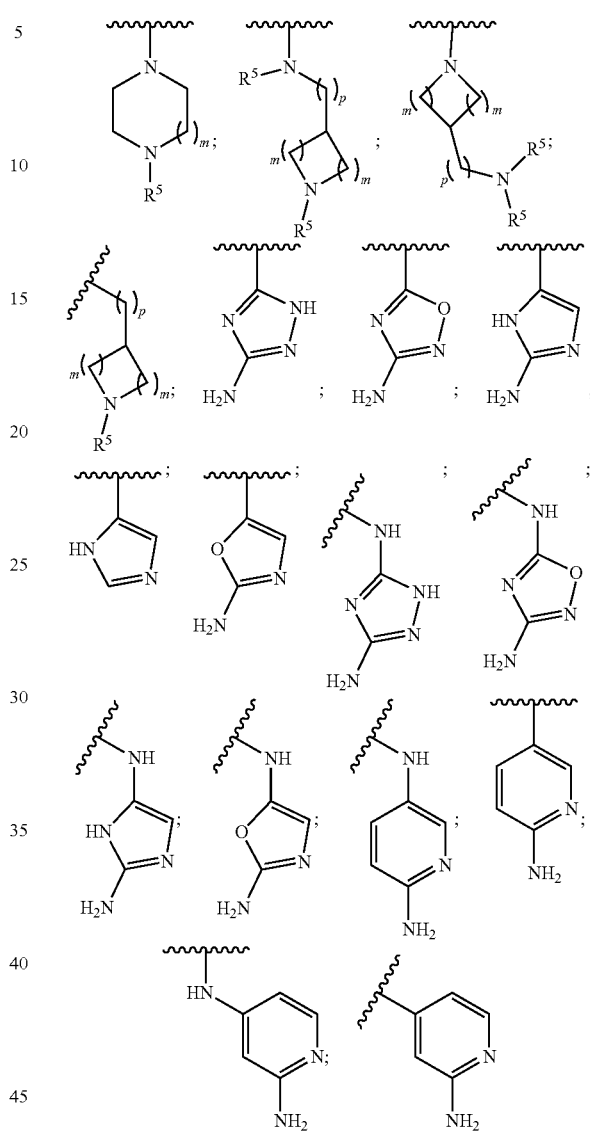

m = 1,2
p = 0, 1, 2, 3

Finally, still referring to Formula IV, Y may be selected from N and CH.

The exemplary therapeutic agents described above are fructokinase inhibitors that may be administered to treat or prevent metabolic disorders and diseases. Furthermore, some of the crystalline forms for the compounds according to various embodiments may exist as polymorphs and as such are intended to be included in the within the scope of this disclosure. In addition, some of the compounds according to various embodiments may form solvates with water (i.e., hydrates) or common organic solvents, and such solvates are also intended to be encompassed within the scope of this disclosure.

Table 1 provides a list of specific species of exemplary therapeutic agents. Table 1 includes the IUPAC Name for each compound as well as a mass-to-charge ratio (m/z) for each compound. As used herein, the term "mass-to-charge ratio" refers to a dimensionless quantity formed by dividing the ratio of the mass of an ion to the unified atomic mass unit, by its charge number (regardless of sign).

TABLE 1

| Compound | TEMP SPR CROSS REF | Structure | IUPAC Name | M/Z |
|---|---|---|---|---|
| C-1 | SPR439 | 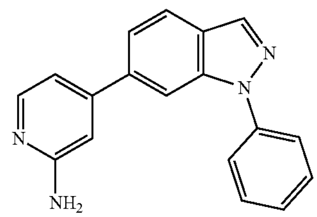 [SMILES: Nc1cc(-c2ccc3cnn(-c4ccccc4)c3c2)ccn1] | 4-(1-phenyl-1H-indazol-6-yl)pyridin-2-amine | 287 |
| C-2 | SPR306 | 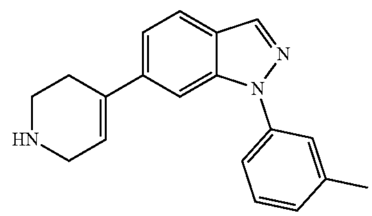 [SMILES: Cc1cccc(-n2ncc3ccc(C4=CCNCC4)cc32)c1] | 6-(1,2,3,6-tetrahydropyridin-4-yl)-1-(m-tolyl)-1H-indazole | 290 |
| C-3 | SPR356 | 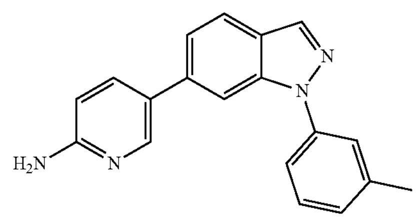 [SMILES: Cc1cccc(-n2ncc3ccc(-c4ccc(N)nc4)cc32)c1] | 5-(1-(m-tolyl)-1H-indazol-6-yl)pyridin-2-amine | 301 |
| C-4 | SPR361 | 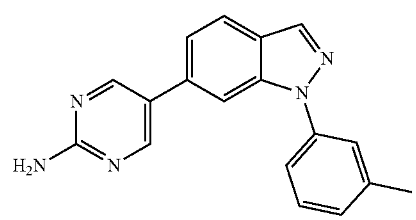 [SMILES: Cc1cccc(-n2ncc3ccc(-c4cnc(N)nc4)cc32)c1] | 5-(1-(m-tolyl)-1H-indazol-6-yl)pyrimidin-2-amine | 302 |
| C-5 | SPR366 | 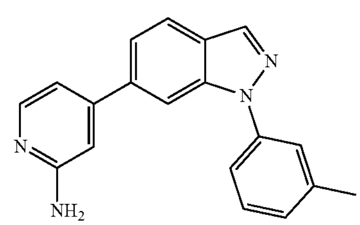 | 4-(1-(m-tolyl)-1H-indazol-6-yl)pyridin-2-amine | 301 |
| C-6 | SPR326 | 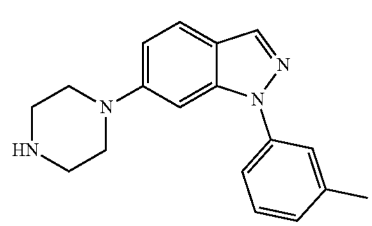 [SMILES: Cc1cccc(-n2ncc3ccc(N4CCNCC4)cc32)c1] | 6-(piperazin-1-yl)-1-(m-tolyl)-1H-indazole | 293 |

TABLE 1-continued

| Compound | TEMP SPR CROSS REF | Structure | IUPAC Name | M/Z |
|---|---|---|---|---|
| C-7 | SPR360 | 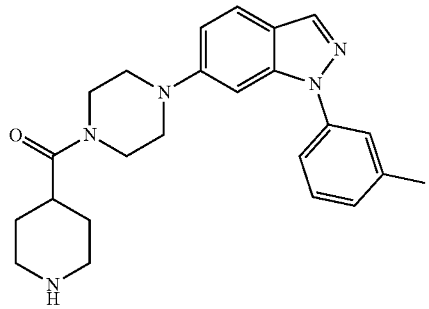 [SMILES: Cc1cccc(-n2ncc3ccc(N4CCN(C(=O)C5CCNCC5)CC4)cc32)c1] | piperidin-4-yl(4-(1-(m-tolyl)-1H-indazol-6-yl)piperazin-1-yl)methanone | 404 |
| C-8 | SPR329 | 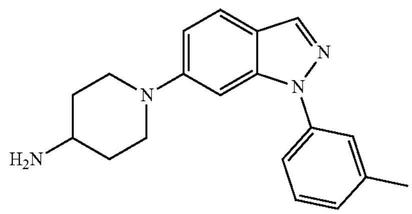 [SMILES: Cc1cccc(-n2ncc3ccc(N4CCC(N)CC4)cc32)c1] | 1-(1-(m-tolyl)-1H-indazol-6-yl)piperidin-4-amine | 307 |
| C-9 | SPR339 | 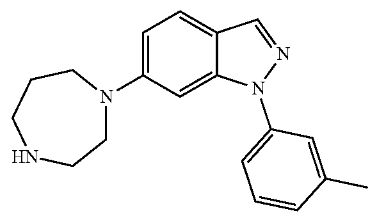 [SMILES: Cc1cccc(-n2ncc3ccc(N4CCCNCC4)cc32)c1] | 6-(1,4-diazepan-1-yl)-1-(m-tolyl)-1H-indazole | 307 |
| C-10 | SPR353 | 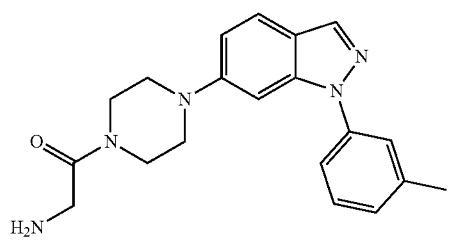 [SMILES: Cc1cccc(-n2ncc3ccc(N4CCN(C(=O)CN)CC4)cc32)c1] | 2-amino-1-(4-(1-(m-tolyl)-1H-indazol-6-yl)piperazin-1-yl)ethan-1-one | 350 |
| C-11 | SPR359 | 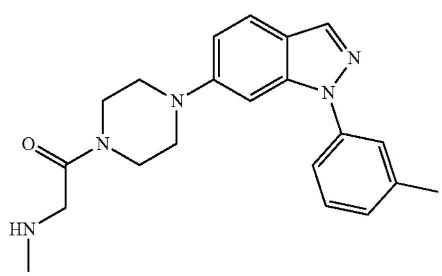 [SMILES: CNCC(=O)N1CCN(c2ccc3cnn(-c4cccc(C)c4)c3c2)CC1] | 2-(methylamino)-1-(4-(1-(m-tolyl)-1H-indazol-6-yl)piperazin-1-yl)ethan-1-one | 364 |
| C-12 | SPR371 | 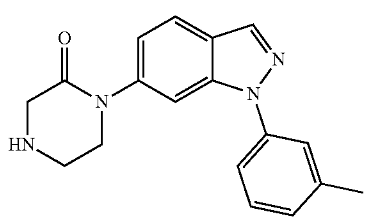 [SMILES: Cc1cccc(-n2ncc3ccc(N4CCNCC4=O)cc32)c1] | 1-(1-(m-tolyl)-1H-indazol-6-yl)piperazin-2-one | 307 |

TABLE 1-continued

| Compound | TEMP SPR CROSS REF | Structure | IUPAC Name | M/Z |
|---|---|---|---|---|
| C-13 | SPR341 | 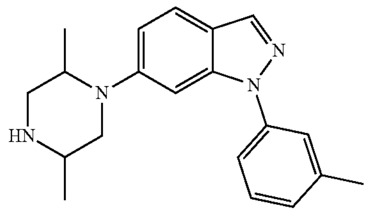 [SMILES: Cc1cccc(-n2ncc3ccc(N4CC(C)NCC4C)cc32)c1] | 6-(2,5-dimethylpiperazin-1-yl)-1-(m-tolyl)-1H-indazole | 321 |
| C-14 | SPR343 | 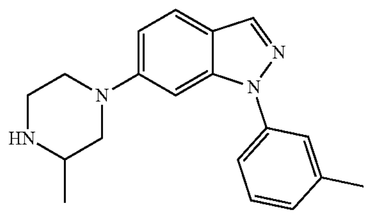 [SMILES: Cc1cccc(-n2ncc3ccc(N4CCNC(C)C4)cc32)c1] | 6-(3-methylpiperazin-1-yl)-1-(m-tolyl)-1H-indazole | 307 |
| C-15 | SPR344 | 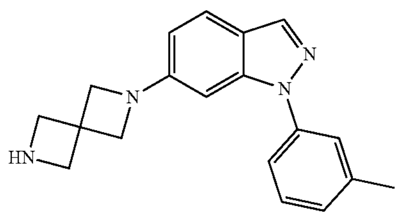 [SMILES: Cc1cccc(-n2ncc3ccc(N4CC5(CNC5)C4)cc32)c1] | 6-(2,6-diazaspiro[3.3]heptan-2-yl)-1-(m-tolyl)-1H-indazole | 305 |
| C-16 | SPR346 | 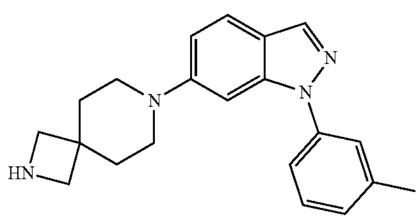 [SMILES: Cc1cccc(-n2ncc3ccc(N4CCC5(CC4)CNC5)cc32)c1] | 7-(1-(m-tolyl)-1H-indazol-6-yl)-2,7-diazaspiro[3.5]nonane | 333 |
| C-17 | SPR367 | 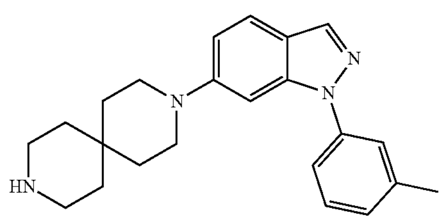 [SMILES: Cc1cccc(-n2ncc3ccc(N4CCC5(CCNCC5)CC4)cc32)c1] | 3-(1-(m-tolyl)-1H-indazol-6-yl)-3,9-diazaspiro[5.5]undecane | 261 |
| C-18 | SPR363 | 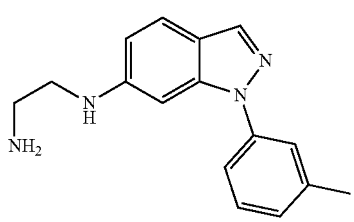 [SMILES: Cc1cccc(-n2ncc3ccc(NCCN)cc32)c1] | N1-(1-(m-tolyl)-1H-indazol-6-yl)ethane-1,2-diamine | 267 |
| C-19 | SPR336 | 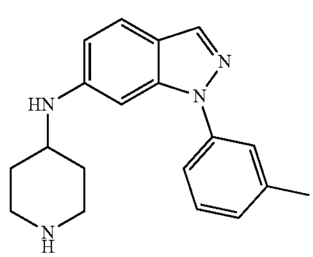 [SMILES: Cc1cccc(-n2ncc3ccc(NC4CCNCC4)cc32)c1] | N-(piperidin-4-yl)-1-(m-tolyl)-1H-indazol-6-amine | 307 |

TABLE 1-continued

| Compound | TEMP SPR CROSS REF | Structure | IUPAC Name | M/Z |
|---|---|---|---|---|
| C-20 | SPR369 | 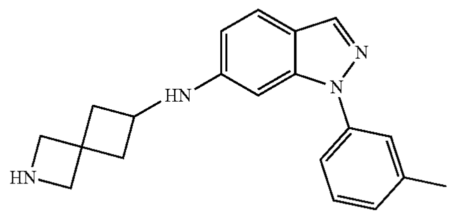 [SMILES: Cc1cccc(-n2ncc3ccc(NC4CC5(CNC5)C4)cc32)c1] | N-(2-azaspiro[3.3]heptan-6-yl)-1-(m-tolyl)-1H-indazol-6-amine | 319 |
| C-21 | SPR358 | 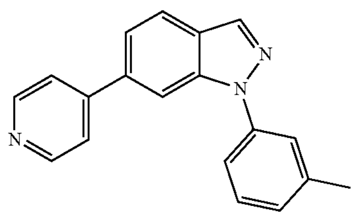 [SMILES: Cc1cccc(-n2ncc3ccc(-c4ccncc4)cc32)c1] | 6-(pyridin-4-yl)-1-(m-tolyl)-1H-indazole | 286 |
| C-22 | SPR355 | 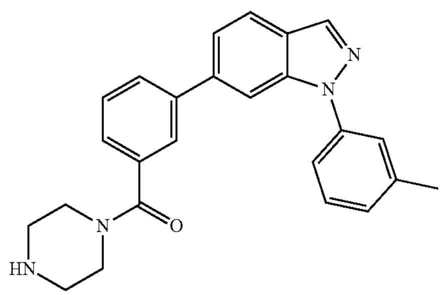 [SMILES: Cc1cccc(-n2ncc3ccc(-c4cccc(C(=O)N5CCNCC5)c4)cc32)c1] | piperazin-1-yl(3-(1-(m-tolyl)-1H-indazol-6-yl)phenyl)methanone | 397 |
| C-23 | SPR357 | 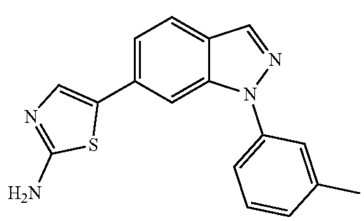 [SMILES: Cc1cccc(-n2ncc3ccc(-c4cnc(N)s4)cc32)c1] | 5-(1-(m-tolyl)-1H-indazol-6-yl)thiazol-2-amine | 307 |
| C-24 | SPR368 | 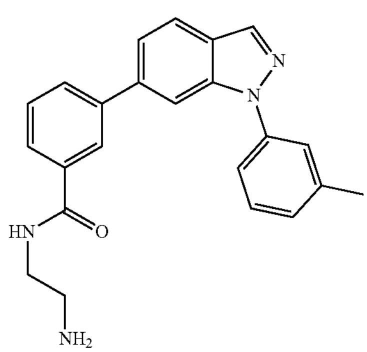 [SMILES: Cc1cccc(-n2ncc3ccc(-c4cccc(C(=O)NCCN)c4)cc32)c1] | N-(2-aminoethyl)-3-(1-(m-tolyl)-1H-indazol-6-yl)benzamide | 371 |
| C-25 | SPR379 | 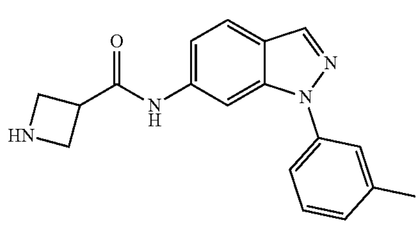 [SMILES: Cc1cccc(-n2ncc3ccc(NC(=O)C4CNC4)cc32)c1] | N-(1-(m-tolyl)-1H-indazol-6-yl)azetidine-3-carboxamide | 307 |

TABLE 1-continued

| Compound | TEMP SPR CROSS REF | Structure | IUPAC Name | M/Z |
|---|---|---|---|---|
| C-26 | SPR437 | 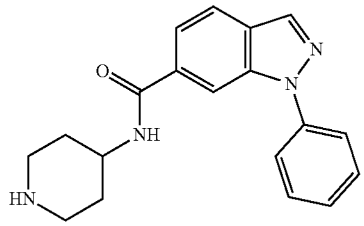 [SMILES: O=C(NC1CCNCC1)c1ccc2cnn(-c3ccccc3)c2c1] | 1-phenyl-N-(piperidin-4-yl)-1H-indazole-6-carboxamide | 321 |
| C-27 | SPR406 | 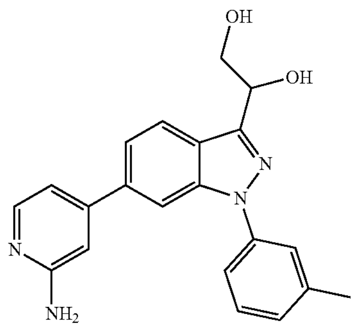 [SMILES: Cc1cccc(-n2nc(C(O)CO)c3ccc(-c4ccnc(N)c4)cc32)c1] | 1-(6-(2-aminopyridin-4-yl)-1-(m-tolyl)-1H-indazol-3-yl)ethane-1,2-diol | 361 |
| C-28 | SPR417 | 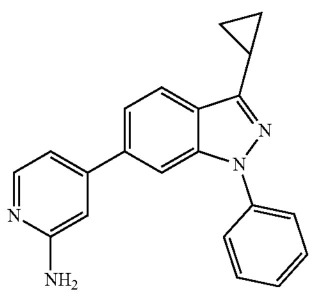 [SMILES: Nc1cc(-c2ccc3c(C4CC4)nn(-c4ccccc4)c3c2)ccn1] | 4-(3-cyclopropyl-1-phenyl-1H-indazol-6-yl)pyridin-2-amine | 327 |
| C-29 | SPR330 | 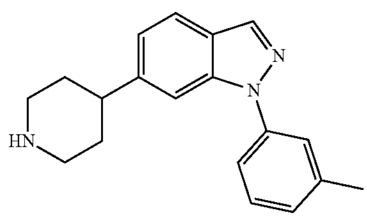 [SMILES: Cc1cccc(-n2ncc3ccc(C4CCNCC4)cc32)c1] | 6-(piperidin-4-yl)-1-(m-tolyl)-1H-indazole | 292 |
| C-30 | SPR327 | 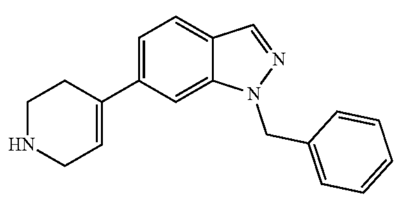 [SMILES: C1=C(c2ccc3cnn(Cc4ccccc4)c3c2)CCNC1] | 1-benzyl-6-(1,2,3,6-tetrahydropyridin-4-yl)-1H-indazole | 290 |
| C-31 | SPR364 | 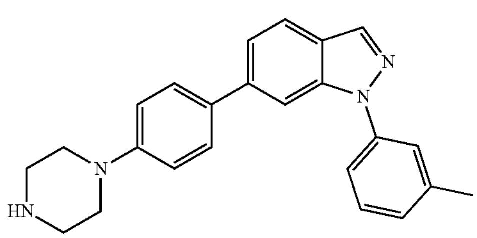 [SMILES: Cc1cccc(-n2ncc3ccc(-c4ccc(N5CCNCC5)cc4)cc32)c1] | 6-(4-(piperazin-1-yl)phenyl)-1-(m-tolyl)-1H-indazole | 369 |

TABLE 1-continued

| Compound | TEMP SPR CROSS REF | Structure | IUPAC Name | M/Z |
|---|---|---|---|---|
| C-32 | SPR435 | 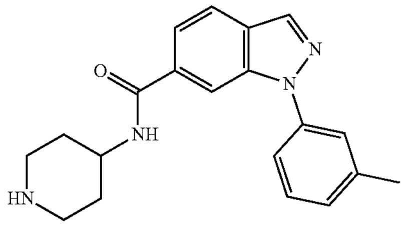 [SMILES: Cc1cccc(-n2ncc3ccc(C(=O)NC4CCNCC4)cc32)c1] | N-(piperidin-4-yl)-1-(m-tolyl)-1H-indazole-6-carboxamide | 335 |
| C-33 | SPR436 | 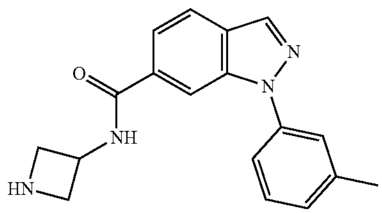 [SMILES: Cc1cccc(-n2ncc3ccc(C(=O)NC4CNC4)cc32)c1] | N-(azetidin-3-yl)-1-(m-tolyl)-1H-indazole-6-carboxamide | 307 |
| C-34 | SPR438 | 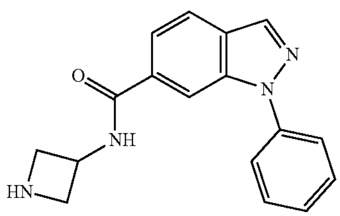 [SMILES: O=C(NC1CNC1)c1ccc2cnn(-c3ccccc3)c2c1] | N-(azetidin-3-yl)-1-phenyl-1H-indazole-6-carboxamide | 293 |
| C-35 | SPR490 | 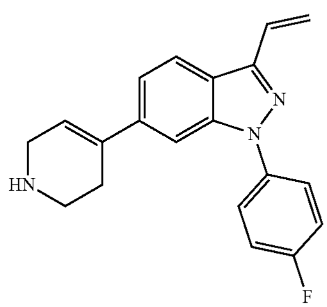 [SMILES: C=Cc1nn(-c2ccc(F)cc2)c2cc(C3=CCNCC3)ccc12] | 1-(4-fluorophenyl)-6-(1,2,3,6-tetrahydropyridin-4-yl)-3-vinyl-1H-indazole | 320 |
| C-36 | | 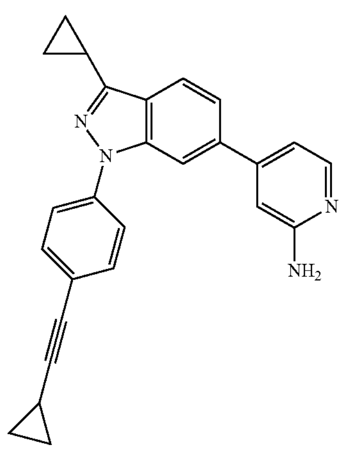 [SMILES: Nc1cc(-c2ccc3c(C4CC4)nn(-c4ccc(C#CC5CC5)cc4)c3c2)ccn1] | 4-(3-cyclopropyl-1-(4-(cyclopropylethynyl)phenyl)-1H-indazol-6-yl)pyridin-2-amine | 390 |

TABLE 1-continued

| Compound | TEMP SPR CROSS REF | Structure | IUPAC Name | M/Z |
|---|---|---|---|---|
| C-37 | | 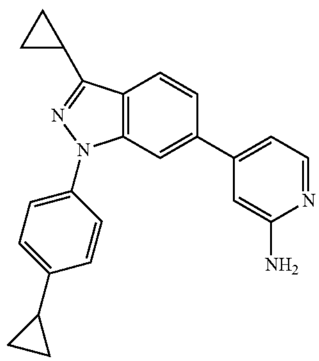 [SMILES: Nc1cc(-c2ccc3c(C4CC4)nn(-c4ccc(C5CC5)cc4)c3c2)ccn1] | 4-(3-cyclopropyl-1-(4-cyclopropylphenyl)-1H-indazol-6-yl)pyridin-2-amine | 366 |
| C-38 | | 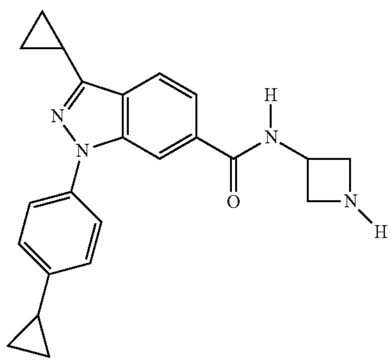 [SMILES: O=C(NC1CNC1)c1ccc2c(C3CC3)nn(-c3ccc(C4CC4)cc3)c2c1] | N-(azetidin-3-yl)-3-cyclopropyl-1-(4-cyclopropylphenyl)-1Hindazole-6-carboxamide | 372 |
| C-39 | | 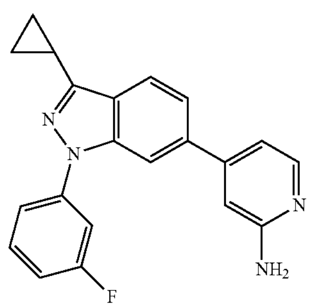 [SMILES: Nc1cc(-c2ccc3c(C4CC4)nn(-c4cccc(F)c4)c3c2)ccn1] | 4-(3-cyclopropyl-1-(3-fluorophenyl)-1H-indazol-6-yl)pyridin-2-amine | 344 |
| C-40 | | 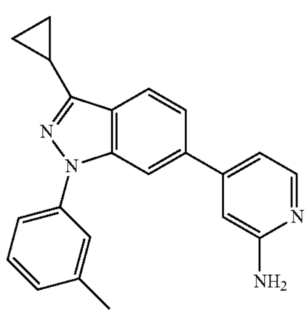 [SMILES: Cc1cccc(-n2nc(C3CC3)c3ccc(-c4ccnc(N)c4)cc32)c1] | 4-(3-cyclopropyl-1-(m-tolyl)-1H-indazol-6-yl)pyridin-2-amine | 340 |

TABLE 1-continued

| Compound | TEMP SPR CROSS REF | Structure | IUPAC Name | M/Z |
|---|---|---|---|---|
| C-41 | | 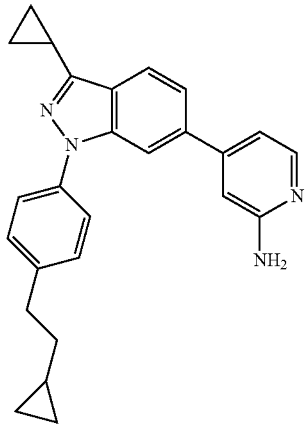 [SMILES: Nc1cc(-c2ccc3c(C4CC4)nn(-c4ccc(CCC5CC5)cc4)c3c2)ccn1] | 4-(3-cyclopropyl-1-(4-(2-cyclopropylethyl)phenyl)-1Hindazol-6-yl)pyridin-2-amine | 395 |
| C-42 | | 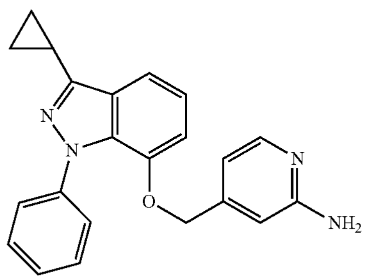 [SMILES: Nc1cc(COc2cccc3c(C4CC4)nn(-c4ccccc4)c23)ccn1] | 4-(((3-cyclopropyl-1-phenyl-1H-indazol-7-yl)oxy)methyl)pyridin-2-amine | 356 |
| C-43 | | 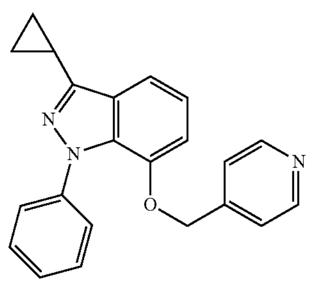 [SMILES: c1ccc(-n2nc(C3CC3)c3cccc(OCc4ccncc4)c32)cc1] | 3-cyclopropyl-1-phenyl-7-(pyridin-4-ylmethoxy)-1Hindazole | 341 |
| C-44 | | 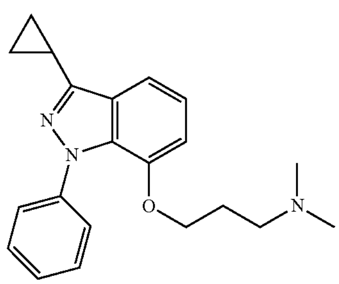 [SMILES: CN(C)CCCOc1cccc2c(C3CC3)nn(-c3ccccc3)c12] | 3-((3-cyclopropyl-1-phenyl-1H-indazol-7-yl)oxy)-N,Ndimethylpropan-1-amine | 335 |
| C-45 | | 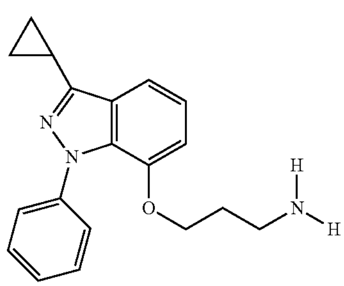 [SMILES: NCCCOc1cccc2c(C3CC3)nn(-c3ccccc3)c12] | 3-((3-cyclopropyl-1-phenyl-1H-indazol-7-yl)oxy)propan-1-amine | 307 |

TABLE 1-continued

| Compound | TEMP SPR CROSS REF | Structure | IUPAC Name | M/Z |
|---|---|---|---|---|
| C-46 | | 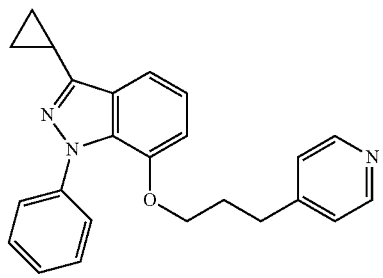 [SMILES: c1ccc(-n2nc(C3CC3)c3cccc(OCCCc4ccncc4)c32)cc1] | 3-cyclopropyl-1-phenyl-7-(3-(pyridin-4-yl)propoxy)-1H-indazole | 369 |
| C-47 | | 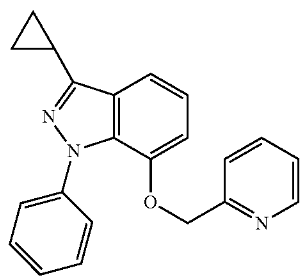 [SMILES: c1ccc(-n2nc(C3CC3)c3cccc(OCc4ccccn4)c32)cc1] | 3-cyclopropyl-1-phenyl-7-(pyridin-2-ylmethoxy)-1H-indazole | 341 |
| C-48 | | 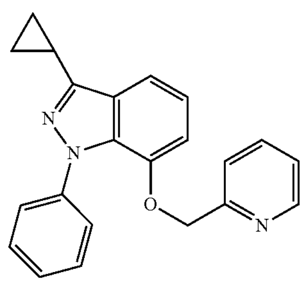 [SMILES: c1ccc(-n2nc(C3CC3)c3cccc(OCc4ccccn4)c32)cc1] | 2-((3-cyclopropyl-1-phenyl-1H-indazol-7-yl)oxy)-N,Ndimethylethan-1-amine | 321 |
| C-49 | | 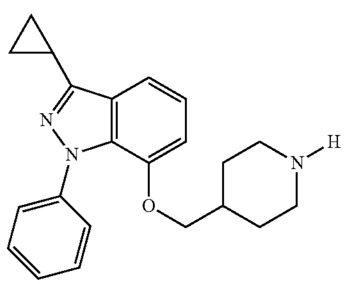 [SMILES: c1ccc(-n2nc(C3CC3)c3cccc(OCC4CCNCC4)c32)cc1] | 3-cyclopropyl-1-phenyl-7-(piperidin-4-ylmethoxy)-1Hindazole | 347 |
| C-50 | | 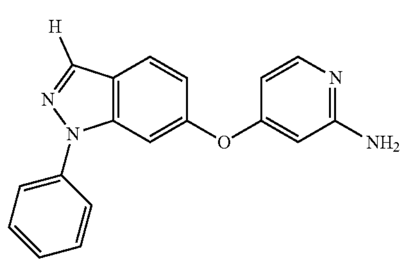 [SMILES: Nc1cc(Oc2ccc3cnn(-c4ccccc4)c3c2)ccn1] | 4-((1-phenyl-1H-indazol-6-yl)oxy)pyridin-2-amine | 302 |

TABLE 1-continued

| Compound | TEMP SPR CROSS REF | Structure | IUPAC Name | M/Z |
|---|---|---|---|---|
| C-51 | | 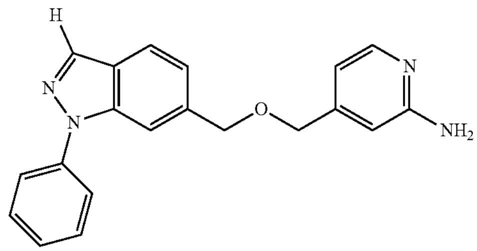 [SMILES: Nc1cc(COCc2ccc3cnn(-c4ccccc4)c3c2)ccn1] | 4-(((1-phenyl-1H-indazol-6-yl)methoxy)methyl)pyridin-2-amine | 330 |
| C-52 | | 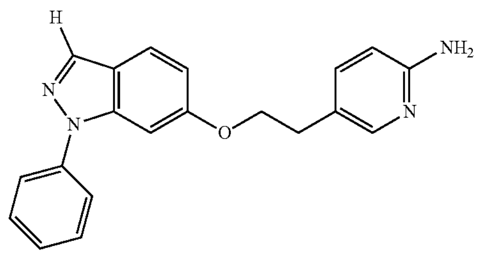 [SMILES: Nc1ccc(CCOc2ccc3cnn(-c4ccccc4)c3c2)cn1] | 5-(2-((1-phenyl-1H-indazol-6-yl)oxy)ethyl)pyridin-2-amine | 330 |
| C-53 | | 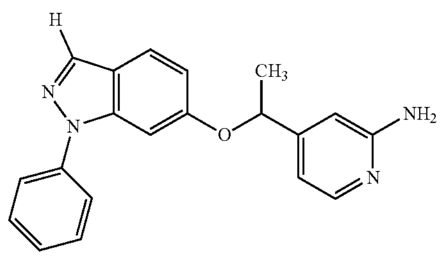 [SMILES: CC(Oc1ccc2cnn(-c3ccccc3)c2c1)c1ccnc(N)c1] | 4-(1-((1-phenyl-1H-indazol-6-yl)oxy)ethyl)pyridin-2-amine | 330 |
| C-54 | | 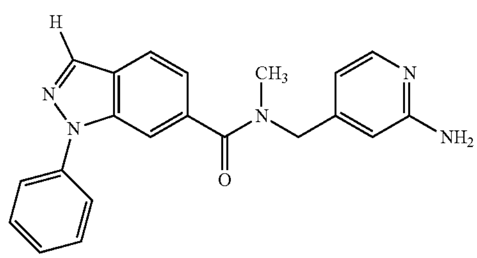 [SMILES: CN(Cc1ccnc(N)c1)C(=O)c1ccc2cnn(-c3ccccc3)c2c1] | N-((2-aminopyridin-4-yl)methyl)-N-methyl-1-phenyl-1H-indazole-6-carboxamide | 357 |
| C-55 | | 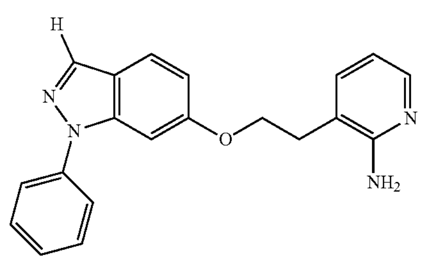 [SMILES: Nc1ncccc1CCOc1ccc2cnn(-c3ccccc3)c2c1] | 3-(2-((1-phenyl-1H-indazol-6-yl)oxy)ethyl)pyridin-2-amine | 330 |
| C-56 | | 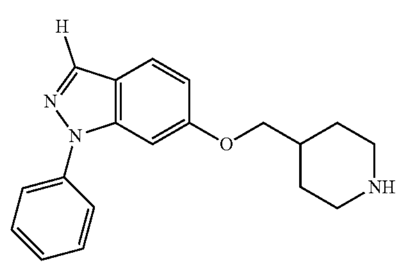 [SMILES: c1ccc(-n2ncc3ccc(OCC4CCNCC4)cc32)cc1] | 1-phenyl-6-(piperidin-4-ylmethoxy)-1H-indazole | 307 |

TABLE 1-continued

| Compound | TEMP SPR CROSS REF | Structure | IUPAC Name | M/Z |
|---|---|---|---|---|
| C-57 | | 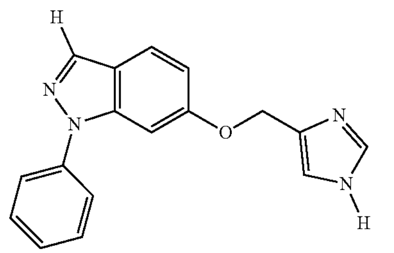 [SMILES: c1ccc(-n2ncc3ccc(OCc4c[nH]cn4)cc32)cc1] | 6-((1H-imidazol-4-yl)methoxy)-1-phenyl-1Hindazole | 290 |
| C-58 | | 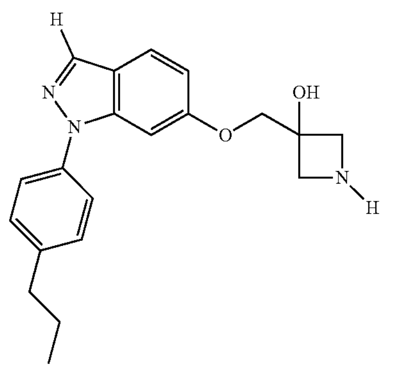 [SMILES: CCCc1ccc(-n2ncc3ccc(OCC4(O)CNC4)cc32)cc1] | 3-(((1-(4-propylphenyl)-1Hindazol-6-yl)oxy)methyl)azetidin-3-ol | 337 |
| C-59 | | 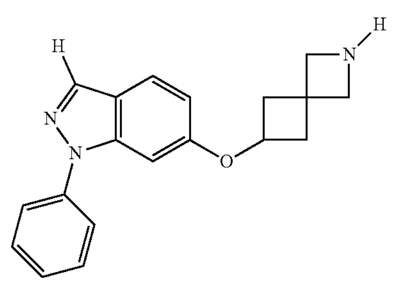 [SMILES: c1ccc(-n2ncc3ccc(OC4CC5(CNC5)C4)cc32)cc1] | 6-((2-azaspiro[3.3]heptan-6-yl)oxy)-1-phenyl-1H-indazole | 305 |
| C-60 | | 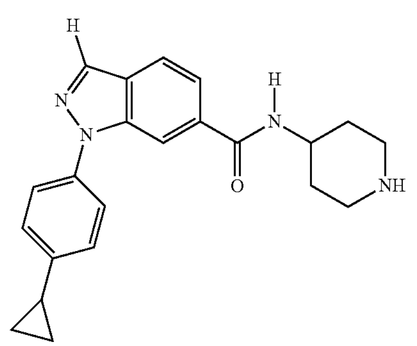 [SMILES: O=C(NC1CCNCC1)c1ccc2cnn(-c3ccc(C4CC4)cc3)c2c1] | 1-(4-cyclopropylphenyl)-N-(piperidin-4-yl)-1H-indazole-6-carboxamide | 360 |
| C-61 | | 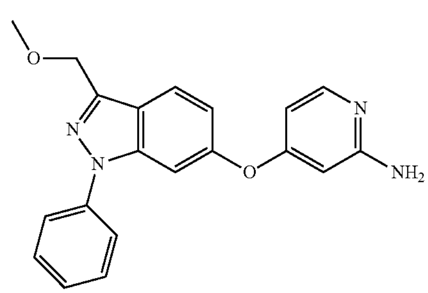 [SMILES: COCc1nn(-c2ccccc2)c2cc(Oc3ccnc(N)c3)ccc12] | 4-((3-(methoxymethyl)-1-phenyl-1H-indazol-6-yl)oxy)pyridin-2-amine | 346 |

TABLE 1-continued

| Compound | TEMP SPR CROSS REF | Structure | IUPAC Name | M/Z |
|---|---|---|---|---|
| C-62 | | 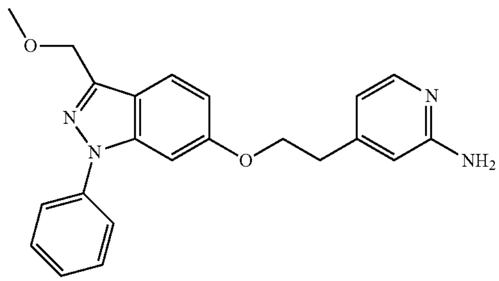 [SMILES: COCc1nn(-c2ccccc2)c2cc(OCCc3ccnc(N)c3)ccc12] | 4-(2-((3-(methoxymethyl)-1-phenyl-1H-indazol-6-yl)oxy)ethyl)pyridin-2-amine | 374 |
| C-63 | | 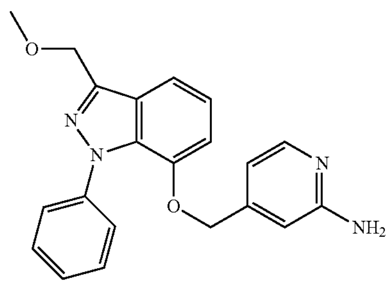 [SMILES: COCc1nn(-c2ccccc2)c2c(OCc3ccnc(N)c3)cccc12] | 4-(((3-(methoxymethyl)-1-phenyl-1H-indazol-7-yl)oxy)methyl)pyridin-2-amine | 360 |
| C-64 | | 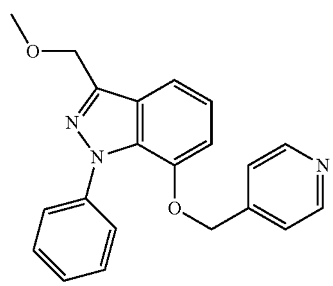 [SMILES: COCc1nn(-c2ccccc2)c2c(OCc3ccncc3)cccc12] | 3-(methoxymethyl)-1-phenyl-7-(pyridin-4-ylmethoxy)-1Hindazole | 345 |
| C-65 | | 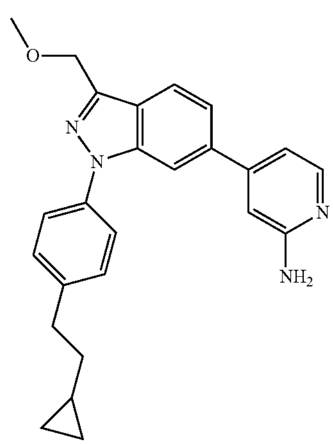 [SMILES: COCc1nn(-c2ccc(CCC3CC3)cc2)c2cc(-c3ccnc(N)c3)ccc12] | 4-(1-(4-(2-cyclopropylethyl)phenyl)-3-(methoxymethyl)-1H-indazol-6-yl)pyridin-2-amine | 398 |

TABLE 1-continued

| Compound | TEMP SPR CROSS REF | Structure | IUPAC Name | M/Z |
|---|---|---|---|---|
| C-66 | | 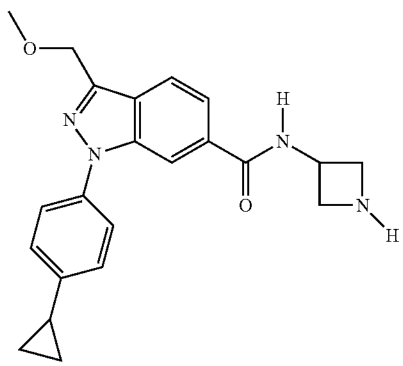 [SMILES: COCc1nn(-c2ccc(C3CC3)cc2)c2cc(C(=O)NC3CNC3)ccc12] | N-(azetidin-3-yl)-1-(4-cyclopropylphenyl)-3-(methoxymethyl)-1Hindazole-6-carboxamide | 376 |
| C-67 | | 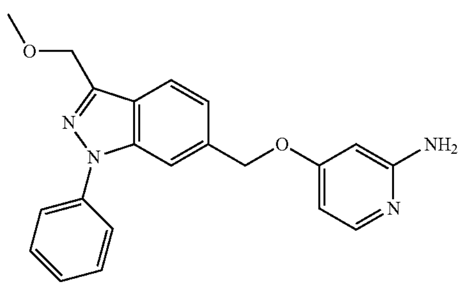 [SMILES: COCc1nn(-c2ccccc2)c2cc(COc3ccnc(N)c3)ccc12] | 4-((3-(methoxymethyl)-1-phenyl-1H-indazol-6-yl)methoxy)pyridin-2-amine | 360 |
| C-68 | | 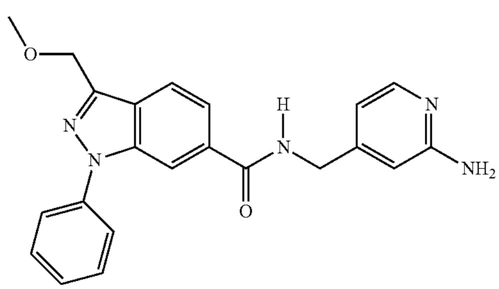 [SMILES: COCc1nn(-c2ccccc2)c2cc(C(=O)NCc3ccnc(N)c3)ccc12] | N-((2-aminopyridin-4-yl)methyl)-3-(methoxymethyl)-1-phenyl-1H-indazole-6-carboxamide | 387 |
| C-69 | | 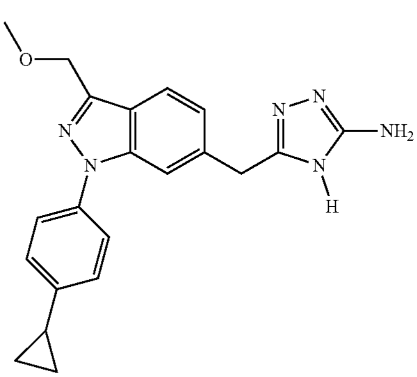 [SMILES: COCc1nn(-c2ccc(C3CC3)cc2)c2cc(Cc3nnc(N)[nH]3)ccc12] | 5-((1-(4-cyclopropylphenyl)-3-(methoxymethyl)-1Hindazol-6-yl)methyl)-4H-1,2,4-triazol-3-amine | 374 |

TABLE 1-continued

| Compound | TEMP SPR CROSS REF | Structure | IUPAC Name | M/Z |
|---|---|---|---|---|
| C-70 | | 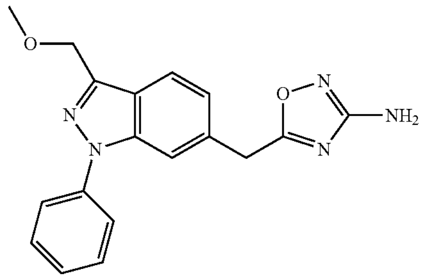 [SMILES: COCc1nn(-c2ccccc2)c2cc(Cc3nc(N)no3)ccc12] | 5-((3-(methoxymethyl)-1-phenyl-1H-indazol-6-yl)methyl)-1,2,4-oxadiazol-3-amine | 335 |
| C-71 | SPR497 | 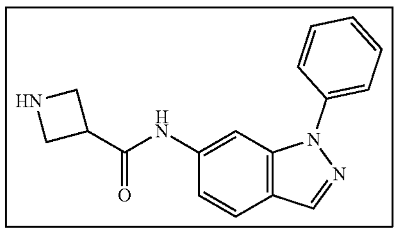 [SMILES: O=C(Nc1ccc2cnn(-c3ccccc3)c2c1)C1CNC1] | | |
| C-72 | SPR533 | 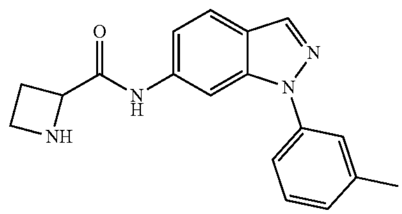 [SMILES: Cc1cccc(-n2ncc3ccc(NC(=O)C4CCN4)cc32)c1] | | |
| C73 | SPR535 | 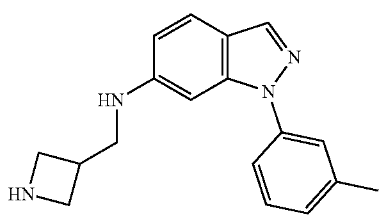 [SMILES: Cc1cccc(-n2ncc3ccc(NCC4CNC4)cc32)c1] | | |
| C74 | SPR539 | 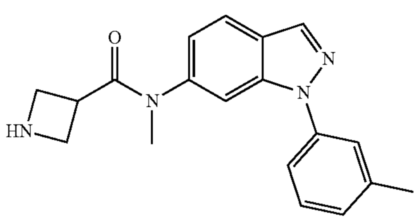 [SMILES: Cc1cccc(-n2ncc3ccc(N(C)C(=O)C4CNC4)cc32)c1] | | |

Definitions

The term "prevent" or "preventions" as used herein means either 1) the reduction in frequency or severity of symptoms commonly associated with the disorder; or 2) a delay or avoidance of additional symptoms associated with the condition or disease, or complete prevention of the disease. One skilled in the art will recognize that wherein the various embodiments are directed to methods of prevention, a subject in need thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "treat" or "treatment" as used herein means administering a compound to manage the symptoms or underlying cause of a condition with the goal of reducing symptoms or signs of the disease and either to prevent or to slow progression, to arrest or potentially to reverse manifestations of the disease, or to inhibit the underlying mechanism(s) causing the disease.

"Exemplary Therapeutic Agents" as used herein refers to any compound according to Formulas I, II, III, or IV defined above. Exemplary Therapeutic Agents include pharmaceutical salts of any of the compounds of Formulas I, II, III or IV. "Ketohexokinase mediated disease and/or disorders" include, but are not limited to, obesity or elevated abdominal circumference, elevated glucose levels, glucose intolerance, impaired fasting glucose levels (serum glucose 100-125 mg/dl), insulin resistance (as noted by elevated fasting plasma insulin levels or elevated HOMA index), Type I diabetes mellitus, Type II diabetes mellitus, Metabolic Syndrome X, lipid disorders characterized by elevated LDL, low HDL, or hypertriglyceridemia, and hypertension (defined as >130/85 mm Hg). Preferably, the ketohexokinase mediated disorder is selected from the group consisting of obesity, Type II diabetes mellitus and Metabolic Syndrome X.

Additional exemplary disorders include fatty liver disease (both nonalcoholic and alcoholic) as well as more progressive forms of nonalcoholic fatty liver disease (including steatohepatitis and cirrhosis). Other exemplary disorders include acute kidney disease due to ischemia, contrast, diabetes, or heat stress, as well as both diabetic and non-diabetic chronic kidney disease.[5, 8, 9] Ischemia to other organs, including the heart, are also mediated by fructokinase and may be associated with benefit by inhibitors according to various embodiments.[10]

Hereditary fructose intolerance is a rare orphan disease that is also amenable to fructokinase therapy. HFI can be associated with hypoglycemia, seizures, lactic acidosis with acute fructose ingestion, and with chronic liver and kidney disease later in life. These conditions can be prevented with fructokinase inhibitor(s)[7].

Other conditions potentially amenable to fructokinase inhibition therapy for both prevention and treatment could include gastrointestinal disorders (celiac disease and Crohn's disease), food-induced allergies (including anaphylaxis), neurological disorders (mania, Alzheimers and attention deficit disorder), and gout or hyperuricemia. Fructokinase inhibition may also benefit subjects with obesity, either by helping prevent weight gain, or as a way to prevent rebound of weight following dieting. Inhibitors for fructokinase may also help prevent craving to sugar, HFCS or other compounds that contain fructose. Fructokinase inhibitors may also block weight gain from foods that do not contain fructose (such as nonfructose containing carbohydrates or salt) as they inhibit endogenous fructose that is generated in response to eating these foods. The terms "subject," "individual," "host," and "patient," are used interchangeably herein to refer to an animal being treated with one or more exemplary agents as taught herein, including, but not limited to, simians, humans, avians, felines, canines, equines, rodents, bovines, porcines, ovines, caprines, mammalian farm animals, mammalian sport animals, and mammalian pets. A suitable subject for various embodiments can be any animal, preferably a human, that is suspected of having, has been diagnosed as having, or is at risk of developing a disease that can be ameliorated, treated or prevented by administration of one or more exemplary agents.

As used herein "therapeutically effective amount" refers to an amount which, when administered in a proper dosing regimen, is sufficient to reduce or ameliorate the severity, duration, or progression of the disorder being treated, prevent the advancement of the disorder being treated, cause the regression of the disorder being treated, or enhance or improve the prophylactic or therapeutic effect(s) of another therapy. The full therapeutic effect does not necessarily occur by administration of one dose and may occur only after administration of a series of doses. Thus, a therapeutically effective amount may be administered in one or more administrations per day for successive days.

As used herein, the terms "administering" or "administration" of an agent, drug, or peptide to a subject includes any route of introducing or delivering to a subject a compound to perform its intended function. The administering or administration can be carried out by any suitable route, including orally, intranasally, parenterally (intravenously, intramuscularly, intraperitoneally, or subcutaneously), rectally, or topically. Administering or administration includes self-administration and the administration by another.

As used herein, the terms "co-administered, "co-administering," or "concurrent administration", when used, for example with respect to administration of an exemplary therapeutic agent with another exemplary therapeutic agent, or a conjunctive agent along with administration of an exemplary therapeutic agent refers to administration of the exemplary therapeutic agent and the other exemplary therapeutic agent and/or conjunctive agent such that both can simultaneously achieve a physiological effect. The two agents, however, need not be administered together. In certain embodiments, administration of one agent can precede administration of the other, however, such co-administering typically results in both agents being simultaneously present in the body (e.g. in the plasma) of the subject.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, any exemplified reaction step(s) may be performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example, wherein two steps of a process recite an organic or inorganic base as a reagent, the organic or inorganic base selected for the first step may be the same or different than the organic or inorganic base of the second step. Further, one skilled in the art will recognize that wherein a reaction step of various embodiments may be carried out in a variety of solvents or solvent systems, said reaction step may also be carried out in a mixture of the suitable solvents or solvent systems.

Examples of suitable solvents, bases, reaction temperatures, and other reaction parameters and components are provided in the detailed description which follows herein. One skilled in the art will recognize that the listing of specific examples is not intended, and should not be construed, as limiting in any way the various embodiments set forth in the claims which follow thereafter.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

For use in medicine, the salts of the compounds of various embodiments refer to non-toxic "pharmaceutically acceptable salts." Other salts may, however, be useful in the preparation of compounds according to various embodiments or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid, or phosphoric acid. Furthermore, where the compounds of various embodiments carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid, and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine, and zinc hydroxide.

Various embodiments may include prodrugs of the compounds according to other embodiments. As used herein the term "prodrug" refers to a biologically inactive compound that can be metabolized in the body to produce a drug. In general, such prodrugs may be functional derivatives of the compounds which are readily convertible in vivo into the required compound. Thus, in the methods of treatment of various embodiments, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are well-known to those of ordinary skill in the art.

Pharmaceutical Compositions and Dosing

The exemplary therapeutic compounds according to various embodiments are useful in the treatment of disorders mediated by ketohexokinase, as may be determined, for example, according to the procedures described in the Biological Example, which follows herein. Various embodiments may, therefore, provide a method of treating disorders mediated by ketohexokinase comprising administering to a subject in need thereof a therapeutically effective amount of any of the compounds of formulas I, II, III, or IV as herein defined. According to various embodiments, a compound of formula I, II, III, or IV may be administered in a therapeutically effective amount in the range of from about 0.01 mg/kg of body weight to about 20 mg/kg of body weight, or any amount or range therein. For example, a compound of formula I, II, III, or IV may be administered in a therapeutically effective amount in the range having a lower limit and/or an upper limit. The range can include or exclude the lower limit and/or the upper limit. The lower limit and/or upper limit can be selected from about 0.01, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, and 20 mg/kg of body weight. For example, according to certain embodiments, a compound of formula I, II, III, or IV may be administered in a therapeutically effective amount in the range of from about 1 mg/kg of body weight to about 15 mg/kg of body weight, or any combination of lower limits and upper limits described.

Various embodiments may further comprise pharmaceutical compositions containing one or more compounds of formulas I, II, III, or IV with a pharmaceutically acceptable carrier. Pharmaceutical compositions containing one or more of the compounds according to various embodiments as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus, for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions according to various embodiments, one or more compounds of according to various embodiments as the active ingredient may be intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents, and the like; for solid oral preparations such as, for example, powders, capsules, caplets, gelcaps and tablets, suitable carriers and additives include starches, sugars, diluents, granulating agents, lubricants, binders, disintegrating agents, and the like. Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions according to various embodiments may contain an active ingredient in an amount, per unit dosage unit, e.g., tablet, capsule, powder, injection, suppository, teaspoonful and the like, of from about 0.01 to about 1500 mg or any amount or range therein. For example, the pharmaceutical compositions according to various embodiments may contain an active ingredient in an amount, per unit dosage unit, e.g., tablet, capsule, powder, injection, suppository, teaspoonful and the like, within a range having a lower limit and/or an upper limit. The range may include or exclude the lower limit and/or the upper limit. The lower limit and/or upper limit can be selected from about 0.01, 0.5, 1, 5, 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, and 2000 mg. For example, according to certain embodiments, the pharmaceutical compositions according to various embodiments may contain an active ingredient in an amount, per unit dosage unit, e.g., tablet, capsule, powder, injection, suppository, teaspoonful and the like, of from about 0.01 to about 1500 mg, or any combination of lower limits and upper limits described.

Furthermore, the pharmaceutical compositions according to various embodiments may be administered at a dosage of from about 0.01 to about 100 mg/kg/day, or any amount or range therein, preferably from about 0.01 to about 20 mg/kg/day, or any amount or range therein. The dosages, however, may be varied depending upon the requirement of the patients, the severity of the condition being treated, and the compound being employed. The use of either daily administration or post-periodic dosing may be employed. For example, the pharmaceutical compositions according to various embodiments may be administered at a dosage within a range having a lower limit and/or an upper limit. The range may include or exclude the lower limit and/or the upper limit. The lower limit and/or upper limit can be selected from about 0.01, 0.5, 1, 5, 10, 20, 30, 40, 50, 60, 70, 80, 90, 100, 110, 120, 130, 140, 150, 160, 170, 180, 190, and 200 mg/kg/day. For example, according to certain embodiments, the pharmaceutical compositions according to various embodiments may be administered at a dosage of from about 0.5 to about 50 mg/kg/day, or any combination of lower limits and upper limits described.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound according to various embodiments, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 to about 1000 mg of the active ingredient of various embodiments, or any amount or range therein. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of various embodiments may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs, and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, or gelatin.

The method of treating KHK mediated disorders or diseases described in various embodiments may also be carried out using a pharmaceutical composition comprising any of the compounds as defined herein and a pharmaceutically acceptable carrier. The pharmaceutical composition may contain between about 0.01 mg and 1000 mg of the compound, or any amount or range therein; preferably about 0.5 to 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds according to various embodiments may be administered in a single daily dose, or the total daily dosage may be administered in divided doses of two, three or four times daily. Furthermore, compounds according to various embodiments can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents, and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride, and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition according to various embodiments, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Those having ordinary skill in the art will be well-apprised of various pharmaceutically acceptable carriers.

Exemplary therapeutic agents according to various embodiments may be administered in any of the foregoing compositions and according to dosage regimens established in the art whenever treatment of disorders mediated by KHK is required.

The daily dosage of the products may be varied over a wide range from about 0.01 to about 1,500 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 100 mg/kg of body weight per day, or any amount or range therein. Preferably, the range is from about 0.01 to about 50.0 mg/kg of body weight per day, or any amount or range therein. More preferably, from about 0.01 to about 20.0 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet, and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder. One skilled in the art will further recognize that human clinical trials including first-in-human, dose ranging and efficacy trials, in healthy patients and/or those suffering from a given disorder, may be completed according to methods well known in the clinical and medical arts.

The determination of a therapeutically effective dose of the exemplary therapeutic agents is well within the capability of those skilled in the art. A therapeutically effective dose refers to that amount of active ingredient which modulates KHK activity compared to that which occurs in the absence of the therapeutically effective dose. Therapeutic efficacy and toxicity, e.g., ED50 (the dose therapeutically effective in 50% of the population) and LD50 (the dose lethal to 50% of the population), can be determined by standard pharmaceutical procedures in cell cultures or experimental animals. The dose ratio of toxic to therapeutic effects is the therapeutic index, and it can be expressed as the ratio, LD50/ED50.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

In typical embodiments, therapeutic agents according to various embodiments may reduce the activity of a KHK polypeptide by at least about 10-100 percent. Various embodiments may provide a reduction of KHK activity of at least 50, 75, 90, or 100% relative to the absence of the exemplary therapeutic agent. For example, various embodiments may provide a reduction of KHK activity within a range having a lower limit and/or an upper limit. The range may include or exclude the lower limit and/or the upper limit. The lower limit and/or upper limit can be selected from about 10, 15, 20, 25, 30, 35, 40, 45, 50, 55, 60, 65, 70, 75, 80, 85, 90, 95, and 100%. For example, according to certain embodiments, various embodiments may provide a reduction of KHK activity of from about 10 to about 100%, or any combination of lower limits and upper limits described.

Conjunctive Therapeutic Agents

In any of the composition or method embodiments described herein, any of the exemplary therapeutic agents can be co-administered with other appropriate agents (conjunctive agent or conjunctive therapeutic agent) for the treatment or prevention of a target disease. Selection of the appropriate conjunctive agents for use in combination therapy can be made by one of ordinary skill in the art, according to conventional pharmaceutical principles. The combination of therapeutic agents can act synergistically or additively to affect the treatment or prevention of the various disorders described above. Using this approach, one may be able to achieve therapeutic efficacy with lower dosages of each agent, thus reducing the potential for adverse side effects. Any of the therapeutic methods and compositions comprising an exemplary therapeutic agent described herein can be co-administered with another conjunctive agent to a subject in need of such therapy.

Exemplary conjunctive agents that may be formulated and/or administered with any form of an exemplary therapeutic agent as described herein include, but are not limited to, angiotensin-converting enzyme (ACE) inhibitors, aldosterone antagonists, amphetamines, amphetamine-like agents, Angiotensin II receptor antagonists, anti-oxidants, aldose reductase inhibitors, biguanides, sorbitol dehydrogenase inhibitors, thiazolidinediones (glitazones), thiazide and thiazide-like diuretics, triglyceride synthesis inhibitors, inhibitors of adenosine monophosphate deaminase, uric acid lowering agents, e.g., xanthine oxidase inhibitors, and combinations thereof.

Exemplary ACE inhibitors include, but are not limited to, Benazepril (Lotensin), Captopril, Enalapril (Vasotec), Fosinopril, Lisinopril (Prinivil, Zestril), Moexipril (Univasc), Perindopril (Aceon), Quinapril (Accupril), Ramipril (Altace), Trandolapril (Mavik), and combinations thereof.

Exemplary aldosterone antagonists include, but are not limited to, Spironolactone, Eplerenone, Canrenone (canrenoate potassium), Prorenone (prorenoate potassium), Mexrenone (mexrenoate potassium), and combinations thereof.

Exemplary amphetamines include, but are not limited to, amphetamine, methamphetamine, methylphenidate, p-methoxyamphetamine, methylenedioxyamphetamine, 2,5-dimethoxy-4-methylamphetamine, 2,4,5-trimethoxyamphetamine, and 3,4-methylenedioxymethamphetamine, N-ethylamphetamine, fenethylline, benzphetamine, and chlorphentermine as well as the amphetamine compounds of Adderall®; actedron; actemin; adipan; akedron; allodene; alpha-methyl-(.+-.)-benzeneethanamine; alpha-methylbenzeneethanamine; alpha-methylphenethylamine; amfetamine; amphate; anorexine; benzebar; benzedrine; benzyl methyl carbinamine; benzolone; beta-amino propylbenzene; beta-phenylisopropylamine; biphetamine; desoxynorephedrine; dietamine; DL-amphetamine; elastonon; fenopromin; finam; isoamyne; isomyn; mecodrin; monophos; mydrial; norephedrane; novydrine; obesin; obesine; obetrol; octedrine; oktedrin; phenamine; phenedrine; phenethylamine, alpha-methyl-; percomon; profamina; profetamine; propisamine; racephen; raphetamine; rhinalator, sympamine; simpatedrin; simpatina; sympatedrine; and weckamine. Exemplary amphetamine-like agents include but are not limited to methylphenidate. Exemplary compounds for the treatment of ADD include, but are not limited to, methylphenidate, dextroamphetamine/amphetamine, dextroamphetamine, and atomoxetine (non-stimulant).

Exemplary Angiotensin II receptor antagonists or angiotensin receptor blockers (ARBs) include, but are not limited to losartan, irbesartan, olmesartan, candesartan, valsartan, and combinations thereof.

Exemplary anti-oxidant compounds include but are not limited to L-ascorbic acid or L-ascorbate (vitamin C), menaquinone (vitamin K 2), plastoquinone, phylloquinone (vitamin K 1), retinol (vitamin A), tocopherols (e.g., a, f3, y and o-tocotrienols, ubiquinol, and ubiquione (Coenzyme Q10)); and cyclic or polycyclic compounds including acetophenones, anthroquinones, benzoquiones, biflavonoids, catechol melanins, chromones, condensed tannins, coumarins, curcurmins, flavonoids (catechins and epicatechins), hydrolyzable tannins, hydroxycinnamic acids, hydroxybenzyl compounds, isoflavonoids, lignans, naphthoquinones, neolignans, phenolic acids, phenols (including bisphenols and other sterically hindered phenols, aminophenols and thiobisphenols), phenylacetic acids, phenylpropenes, stilbenes and xanthones. Additional cyclic or polycyclic antioxidant compounds include apigenin, auresin, aureusidin, Biochanin A, capsaicin, catechin, coniferyl alcohol, coniferyl aldehyde, cyanidin, daidzein, daphnetin, deiphinidin, emodin, epicatechin, eriodicytol, esculetin, ferulic acid, formononetin, gernistein, gingerol, 3-hydroxybenzoic acid, 4-hydroxybenzoic acid, 3-hydroxycoumarin, juglone, kaemferol, lunularic acid, luteolin, malvidin, mangiferin, 4-methylumbelliferone, mycertin, naringenin, pelargonidin, peonidin, petunidin, phloretin, p-hydroxyacetophenone, (+)-pinoresinol, procyanidin B-2, quercetin, resveratol, resorcinol, rosmaric acid, salicylic acid, scopolein, sinapic acid, sinapoyl-(S)-maleate, sinapyl aldehyde, syrginyl alcohol, telligrandin umbelliferone and vanillin. Antioxidants may also be obtained from plant extracts, e.g., from blackberries, blueberries, black carrots, chokecherries, cranberries, black currants, elderberries, red grapes and their juice, hibiscus, oregano, purple sweet potato, red wine, rosemary, strawberries, tea (e.g., black, green or white tea), and from various plant ingredients as ellagic acid. Exemplary aldose reductase inhibitors include, but are not limited to, epalrestat, ranirestat, fidarestat, sorbinil, and combinations thereof.

Exemplary biguanides include, but are not limited to, metformin, and less rarely used phenformin and buformin, proguanil, and combinations thereof.

Exemplary thiazolidinediones include, but are not limited to, troglitazone, pioglitazone, ciglitazone, rosiglitazone, englitazone, and combinations thereof. Exemplary sorbitol dehydrogenase inhibitors are disclosed in U.S. Pat. Nos. 6,894,047, 6,570,013, 6,294,538, and US Published Patent Application No. 20050020578, the entirety of which are incorporated by reference herein. Exemplary thiazide and thiazide-like diuretics include, but are not limited to, benzothiadiazine derivatives, chlortalidone, metolazone, and combinations thereof. Exemplary triglyceride synthesis inhibitors include, but are not limited to, diglyceride acyltransferase 1 (DGAT-1) inhibitors.

Exemplary uric acid lowering agents include, but are not limited to, xanthine oxidase inhibitors, such as allopurinol, oxypurinol, tisopurine, febuxostat, Topiroxostat, inositols (e.g., phytic acid and myo-inositol), and combinations thereof. An exemplary AMP Deaminase inhibitor would include compounds such as described by Admyre et al.[11]

It is appreciated that suitable conjunctive therapeutic agents for use in various embodiments may also comprise any combinations, prodrugs, pharmaceutically acceptable salts, analogs, and derivatives of the above compounds.

In one embodiment, the exemplary therapeutic agent may be administered to the subject along with one or more other conjunctive therapeutic agents that are active in acute and chronic kidney disease. Exemplary conjunctive therapeutic agents for this use include but are not limited to angiotensin-converting enzyme (ACE) inhibitors, aldosterone antagonists, Angiotensin II receptor antagonists, anti-oxidants, aldose reductase inhibitors, biguanides, sorbitol dehydrogenase inhibitors, thiazolidinediones (glitazones), xanthine oxidase inhibitors, and/or any other agent used to treat acute or chronic kidney disease.

In another embodiment, the therapeutic agent may be administered along with conjunctive therapeutic agents in the treatment of metabolic syndrome, obesity, sugar addiction, sugar craving, and attention deficit disorder. Exemplary conjuvant therapeutic agents for this purpose include Exemplary conjunctive agents that may be formulated and/or administered with any form of an exemplary therapeutic agent as described herein include, but are not limited to, angiotensin-converting enzyme (ACE) inhibitors, aldosterone antagonists, amphetamines, amphetamine-like agents, Angiotensin II receptor antagonists, anti-oxidants, aldose reductase inhibitors, sorbitol dehydrogenase inhibitors, thiazide and thiazide-like diuretics, triglyceride synthesis inhibitors, and/or any other agent used to treat metabolic syndrome, obesity, sugar addiction, sugar craving, and/or attention deficit disorders.

Therapeutic Methods

According to other embodiments, one or more exemplary therapeutic agents are administered in a therapeutically effective amount to treat a KHK mediated disorder or disease in a subject in need. A subject in need is one who has exhibited one or more symptoms of any KHK mediated disorder or disease including presence of a testable physiological marker of the disease in a biological sample (such as blood, serum, saliva or urine), who is at risk of developing a KHK mediated disorder or disease, and/or who has been diagnosed by a medical practitioner to be at risk of developing and/or to have a KHK-mediated disease or disorder.

The one or more exemplary therapeutic agents may be administered in a pharmaceutical composition. The pharmaceutical composition may include one or more therapeutic conjunctive agents.

Synthesis of Exemplary Therapeutic Agents

General schemas for synthesizing a variety of exemplary therapeutic agents are detailed in this section, including schemas for synthesizing: 1,6-Diaryl-3-alkoxymethyl-indazoles, 6-Amido-N-aryl-indazoles, 6-Carboxamido-N-aryl-indazoles, 6-methyleneoxy-N-aryl-indazoles and 6-methyleneamino-N-aryl-indazoles, 6-Heteroayl-N-aryl-indazoles, 6-Heteroarylmethylene-N-aryl-indazoles, and 1,6-Diaryl-indazoles. A person having ordinary skill in the art will understand that the present disclosure is not limited by these exemplary schemas and will be able to readily envision variations.

An exemplary schema for synthesizing 1,6-Diaryl-3-alkoxymethyl-indazoles is shown in R1.

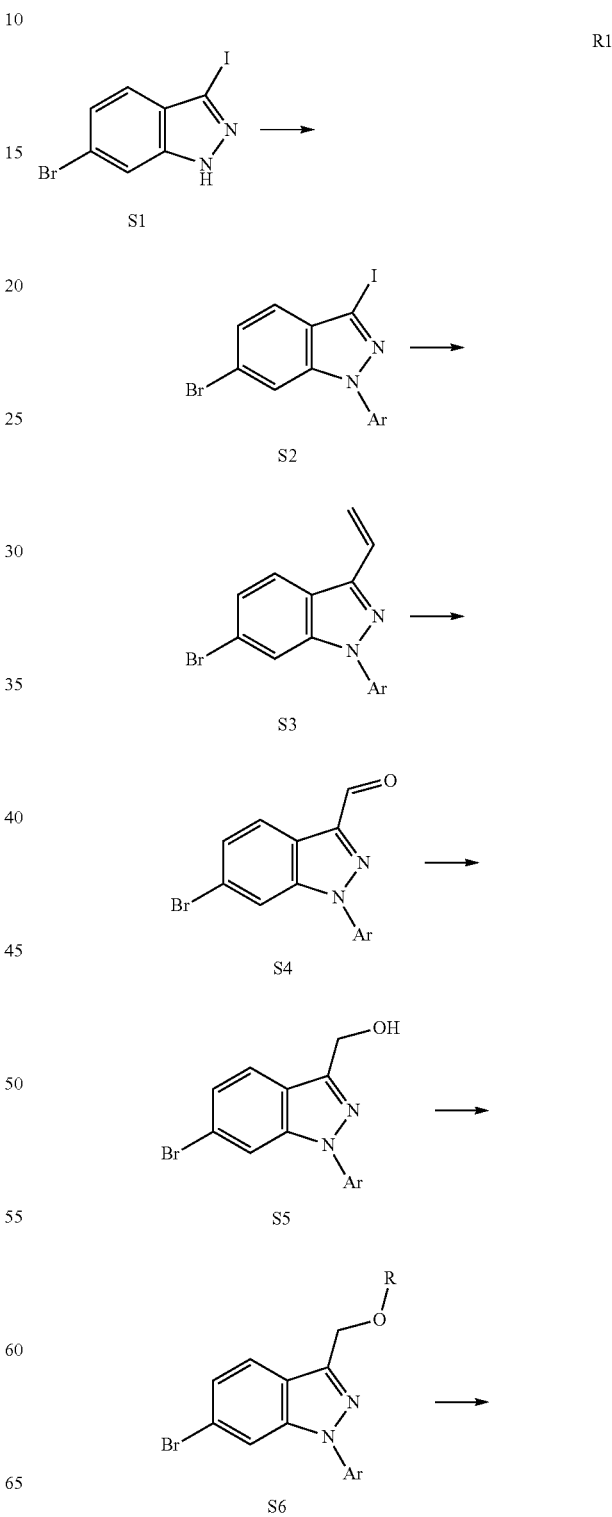

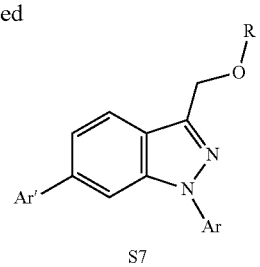

S7

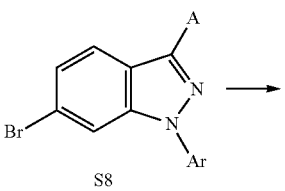

S8

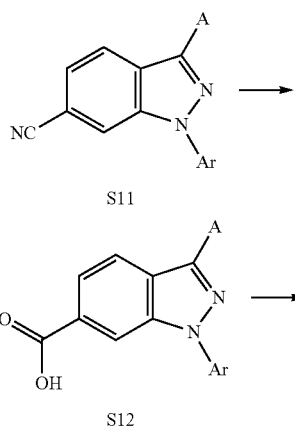

S11

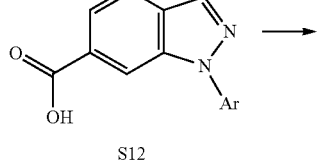

S12

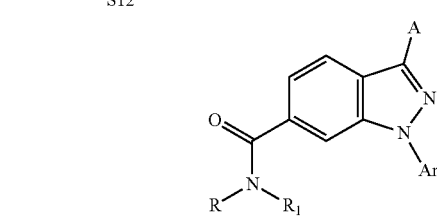

S13

A = H, —CH₂OR, -cyclopropyl

Compounds represented by the structure S7, wherein Ar represents an aryl moiety, may be synthesized starting from 3-iodo-6-bromo-indazole (Si). Coupling with the appropriate arylboronic acid in presence of a catalyst such as copper(II)acetate can give the product of the structure S2, which can then be coupled with vinylboronic acid in presence of a catalyst such as Pd(PPh₃)₄ to give compounds represented by S3. Compounds such as S3 then can be converted to S4 by oxidative cleavage using reagents such as osmium tetraoxide in presence of NaIO₄. A reduction with reducing agents such as sodium borohydride can give compounds represented by structure S5. Alkylation of S5 with an appropriate alkyl halide in the presence of a base can yield compounds of S6. A final coupling with an arly or a heteroaryl boronic acid in the presence of a palladium catalyst can yield the desired series of compounds represented by S7.

An exemplary schema for synthesizing 6-Amido-N-aryl-indazoles is shown in R2.

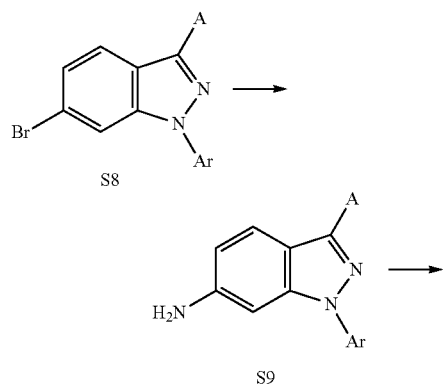

A = H, —CH₂OR, -cyclopropyl

Compounds of structure S9 can be synthesized from the indazoles S8. Coupling using Buchwald conditions with an appropriate amine or aniline and followed by de-protection can give compounds of structure S9. A final acylation with the desired acid moiety can yield compounds of the structure S10.

An exemplary schema for synthesizing 6-Carboxamido-N-aryl-indazoles is shown in R3.

Reacting compounds of structure S8 with CuCN with an appropriate catalyst can give the compounds of type S11. Hydrolysis of compound S11 in the presence of a strong acid will give compounds of the type type represented by S12. A final coupling with the desired amino compound can give the desired carboxamides S13.

An exemplary schema for synthesizing 6-methyleneoxy-N-aryl-indazoles and 6-methyleneamino-N-aryl-indazoles is shown in R4.

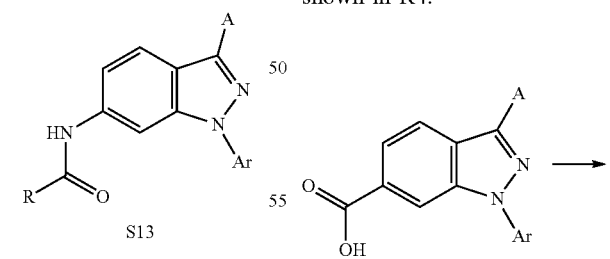

S12

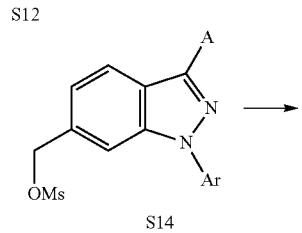

S14

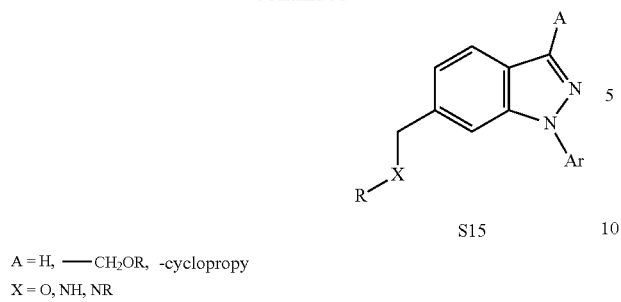

A = H, —CH₂OR, -cyclopropy
X = O, NH, NR

Reduction of compounds represented by S12 with reagents such a lithium aluminum hydride can give the corresponding alcohols which can be converted to the mesylates represented by S14. Compounds represented by S14 can be then reacted by compounds RXH in the presence of a base such as potassium or cesium carbonate to yield the desired compounds represented by S15.

An exemplary schema for synthesizing 6-Heteroayl-N-aryl-indazoles is shown in R5.

R5

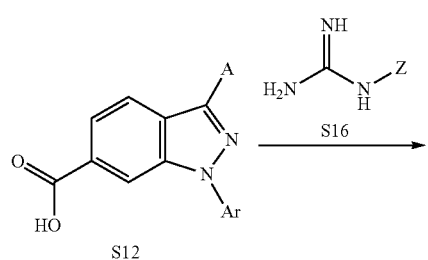

X = NH, O
Z = NH₂, OH

Conversion of S12 to the corresponding ester by using procedures well known such as treating the acid with ethanol in the presence of catalytic acid and subsequently the reaction of the ester with reagents of formula S16 can yield the desired compounds S17.

An exemplary schema for synthesizing 6-Heteroarylm-ethylene-N-aryl-indazoles is shown in R6.

R6

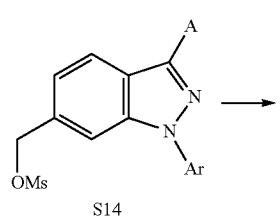

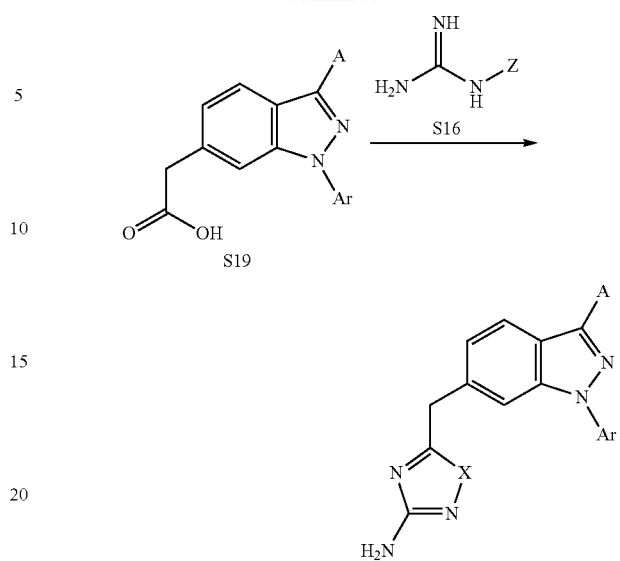

A = H, —CH₂OR, -cyclopropy
X = O, NH
Z = NH₂, OH

Reacting compound S14 with reagent such as sodium cyanide followed by hydrolysis with an acid can lead to the formation of the carboxylic acids S19. Conversion of S19 to the corresponding ester by using procedures well known and subsequently reacting the ester with reagents of formula S16 can yield the desired compounds S20.

An exemplary schema for synthesizing 1,6-Diaryl-indazoles is shown in R7.

R7

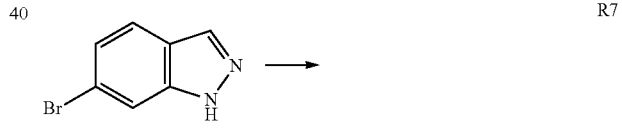

Compounds represented by the structure S23 can be synthesized starting from 6-bromo-indazole S21. Coupling with the appropriate arylboronic acid in presence of a catalyst such as copper(II)acetate can give the product of the structure S22, which can then be coupled with arylboronic acids in presence of a catalyst such as Pd(PPh₃)₄ to give compounds represented by S23.

EXAMPLES

Examples 1-10 demonstrate synthesis protocols of select exemplary therapeutic agents according to various embodiments, more specifically synthesis protocols of N-aryl 6-sub indazole analogs. US Patent Pub. 20110263559 ('559 pub) is cited and incorporated herein by reference in its entirety for further background on synthesis protocols. Those skilled in the art equipped with the teachings herein and the cited '559 pub would appreciate synthesis methods to produce any of the exemplary therapeutic compounds.

Example 11 provides results for select exemplary therapeutic agents according to various embodiments and their half maximal inhibitory concentration ($IC_{50}$) as determined using a 3-step KHK assay. As used herein, "half maximal inhibitory concentration ($IC_{50}$)" is a measure of the effectiveness of a substance in inhibiting a specific biological or biochemical function, more specifically, the $IC_{50}$ is the concentration of an inhibitor where the response (or binding) is reduced by half.

Example 12 describes results observed after injection of fructose into aldoB$^{-/-}$ KO mice that had been injected with compounds according to various embodiments.

Example 1

This example demonstrates the synthesis of 6-bromo-1-(m-tolyl)-1H-indazole (4). A first method, Method A, and a second method, Method B, are shown in reaction schemes R8 and R9.

Method A:

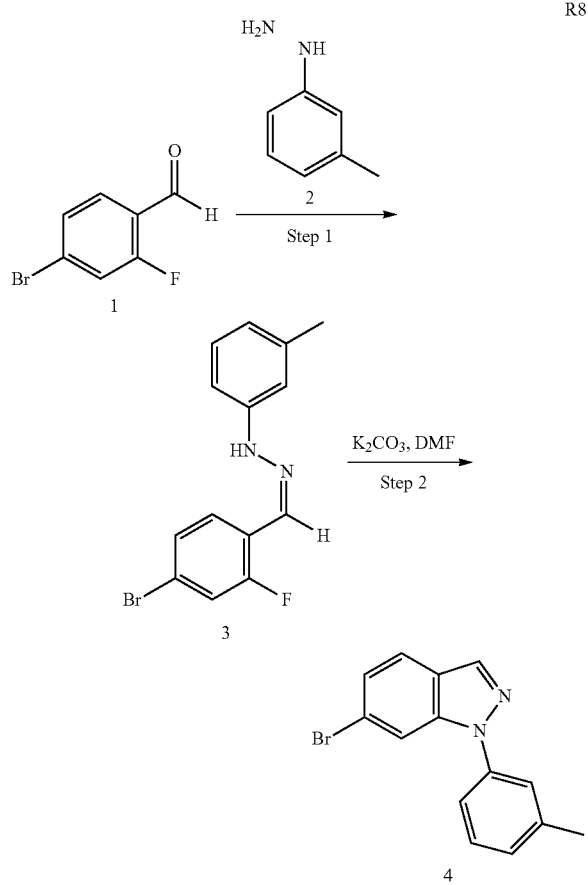

Method B:

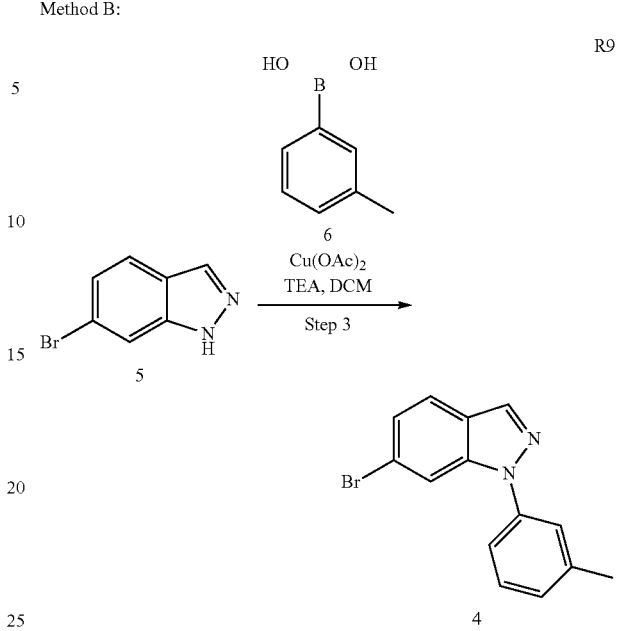

Referring to Reaction Scheme R8, at Step 1:

To a solution of compound 1 (2 g, 9.8 mmol, 1 eq.) in ethanol (30 mL) were added successively tolyl hydrazine 2 (1.32 g, 10.8 mmol, 1.1 eqs.) and PTSA (50 mg). The reaction mixture was heated at 80° C. for 4 hrs. The progress of the reaction was monitored by thin layer chromatography (tlc) taking 1 as a limiting reactant. After completion of reaction, excess of solvent was evaporated under reduced pressure to obtain compound 3 (2.9 g) as a brown semisolid. Compound 3 was taken for the cyclisation step 2 without purification.

Referring to Reaction Scheme R8, at Step 2:

To a solution of compound 3 (2.9 g, 9.4 mmol, 1 eq.) in DMF (30 mL) was added successively $K_2CO_3$ (5.21 g, 37.7 mmol, 4 eqs.). The reaction mixture was heated at 140° C. for 24 hrs. The progress of the reaction was monitored by tlc taking 3 as a limiting reactant. After completion of reaction, reaction mixture was extracted with ethyl acetate (3×100 mL). Combined organic layers were washed with water (50 mL) followed by brine solution (50 mL). The organic layer thus obtained was dried over anhydrous $Na_2SO_4$ and concentrated to get crude product. The crude product was purified via column chromatography using 2% mixture of ethyl acetate in hexane as eluent to obtain 4 as pure compound (1.9 g) as a light brown solid.

Referring to Reaction Scheme R9, at Step 3:

To a solution of compound 5 (1 g, 5.07 mmol, 1 eq.) in DCM (20 mL) were added successively TEA (1.02 g, 10.1 mmol, 2 eqs.) and $Cu(OAc)_2$ (1.37 g, 7.60 mmol, 1.5 eqs.). The reaction mixture was stirred at room temperature for 4 hrs. The progress of the reaction was monitored by tlc taking 6 as a limiting reactant. After completion of reaction, excess of solvent was evaporated under reduced pressure to get crude product. The crude product was purified via column chromatography using 2% mixture of ethyl acetate in hexane as eluent to obtain 4 as pure compound (0.31 g) as a light brown solid.

Example 2

This example demonstrates the synthesis of 4-(1-phenyl-1H-indazol-6-yl)pyridin-2-amine (compound C-1 as shown in Table 1).

A variety of compounds including: C-1, C-2, C-3, C-4, and C-5, as shown in Table 1, may be synthesized following scheme R10 by using appropriate boronic acid/ester reagents.

Example 3

This example demonstrates the synthesis of 6-(piperazin-1-yl)-1-(m-tolyl)-1H-indazole (compound C-6 as shown in Table 1) and piperidin-4-yl(4-(1-(m-tolyl)-1H-indazol-6-yl)piperazin-1-yl)methanone (compound C-7 as shown in Table 1)

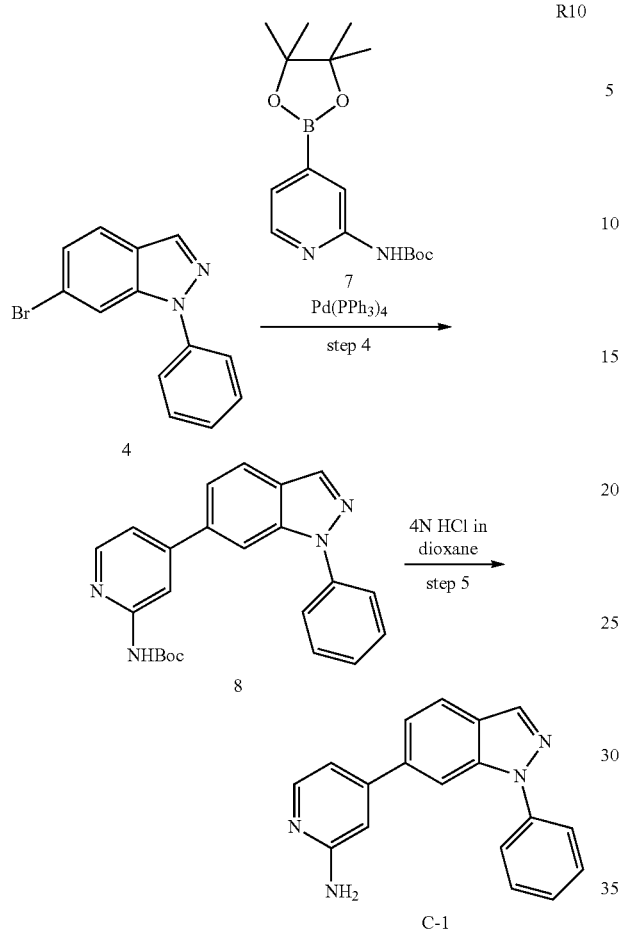

Referring to Reaction Scheme R10, at Step 4:

To a solution of compound 4 (0.1 g, 0.367 mmol, 1 eq.) in dioxane (10 mL) was added successively compound 7 (0.176 g, 0.551 mmol, 1.5 eqs.) and 2 (M) solution of $K_2CO_3$ (0.152 g, 1.101 mmol, 3 eqs.). Degassing was done for 15 min, and then $Pd(PPh_3)_4$ (0.021 g, 0.018 mmol, 0.05 eqs.) was added under inert atmosphere. The reaction mixture was heated at 120° C. for 6 hrs. Excess of solvent was removed under vacuum and the reaction mass was diluted with water and extracted with ethyl acetate (3×30 mL). Combined organic layers were washed with water (30 mL) followed by brine solution (30 mL). The organic layer thus obtained was dried over anhyd. $Na_2SO_4$ and concentrated to get crude product. The crude product was purified via column chromatography using 35% mixture of ethyl acetate in hexane as eluent to obtain 8 as pure compound (81 mg) as a brownish solid.

Referring to Reaction Scheme R10, at Step 5:

To a solution of compound 8 (0.050 g, 0.129 mmol, 1 eq) in DCM (5 mL) was added dioxane HCl (4 M) 0.5 mL at 0° C. temperature. The reaction mixture was stirred at room temperature for 16 hrs. The progress of the reaction was monitored by tlc taking 8 as a limiting reactant. After completion of reaction, excess of solvent was evaporated under reduced pressure to obtain compound 3. Crude compound was purified by column chromatography using 4% mixture of methanol in DCM as eluent to get compound C-5 as shown in Table 1 (0.029 g).

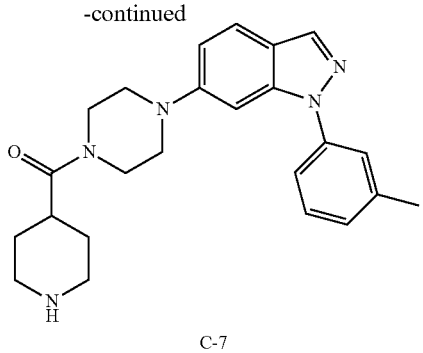

C-7

Referring to Reaction Scheme R11, at Step 6:

To a solution of compound 4 (0.5 g, 1.77 mmol, 1 eq.) in toluene (30 mL) was added successively N-boc piperazine (0.46 g, 2.51 mmol, 1.5 eqs.) and KO'Bu (0.56 g, 5.3 mmol, 3 eqs). Degassing was done for 15 min, and then BINAP (0.1 g, 0.177 mmol, 0.1 eq) and Pd(OAc)$_2$ (0.02 g, 0.088 mmol, 0.05 eq.) were added under inert atmosphere. The reaction mixture was heated at 105° C. for 1.5 hrs. The progress of the reaction was monitored by tlc taking 4 as a limiting reactant. After completion of reaction, reaction mixture was diluted with ethyl acetate (100 mL). Combined organic layers were washed with water (50 mL) followed by brine solution (50 mL). The organic layer thus obtained was dried over anhy. Na$_2$SO$_4$ and concentrated to get crude product. The crude product was purified via column chromatography using 40% mixture of ethyl acetate in hexane as eluent to obtain 9 as pure compound (0.35 g).

Referring to Reaction Scheme R11, at Step 7:

To a solution of compound 9 (40 mg, 0.101 mmol, 1 eq.) in DCM (30 mL) was added dioxane HCl (4 M) 1 mL at 0° C. temperature. The reaction mixture was stirred at room temperature for 6 hrs. The progress of the reaction was monitored by tlc taking 9 as a limiting reactant. After completion of reaction, excess of solvent was evaporated under reduced pressure to obtain crude compound. Crude compound was purified by column chromatography using 4% mixture of methanol in DCM as eluent to get compound C-6 as shown in Table 1 (19 mg).

Referring to Reaction Scheme R11, at Step 8:

To a solution of compound C-6 as shown in Table 1 (0.10 g, 0.342 mmol, 1 eq.) in DMF (5 ml) was added EDC.HCl (0.098 g, 0.513 mmol, 1.5 eqs.) and HOBt (0.078 g, 0.513 mmol, 1.5 eqs.) then stirred at RT for 20 mins. DIPEA (0.132 g, 1.02 mmol, 3 eqs.) and compound 10 (0.117 g, mmol, 0.513 mmol, 1.5 eqs.) were added in to the reaction mixture and stirred at RT for 18 hr. Reaction mass was diluted with DCM and washed with water and brine solution dried over anhydrous sodium sulphate, and then evaporated to obtain a viscous dark brown material. Purification of the solid residue was done by column chromatography in a solvent system of 1% MeOH in DCM to obtain compound 11 (0.090 g).

Referring to Reaction Scheme R11, at Step 9:

To a solution of compound 11 (0.05 g, 0.099 mmol, 1 eq.) in DCM (5 mL) was added dioxane HCl (4 M) 1 mL at 0° C. temperature. The reaction mixture was stirred at room temperature for 6 hrs. The progress of the reaction was monitored by tlc taking 11 as a limiting reactant. After completion of reaction, excess of solvent was evaporated under reduced pressure to obtain compound 3. Crude compound was purified by column chromatography using 4% mixture of methanol in DCM as eluent to get compound C-7 as shown in Table 1 (0.022 g).

A variety of compounds including: C-8, C-9, C-10, C-11, C-12, C-13, C-14, C-15, C-16, C-17, C-18, C-19, and C-20, as shown in Table 1, may be synthesized following scheme R11 by using appropriate amine reagents.

Example 4

This example demonstrates the synthesis of 6-(pyridin-4-yl)-1-(m-tolyl)-1H-indazole (compound C-21 as shown in Table 1).

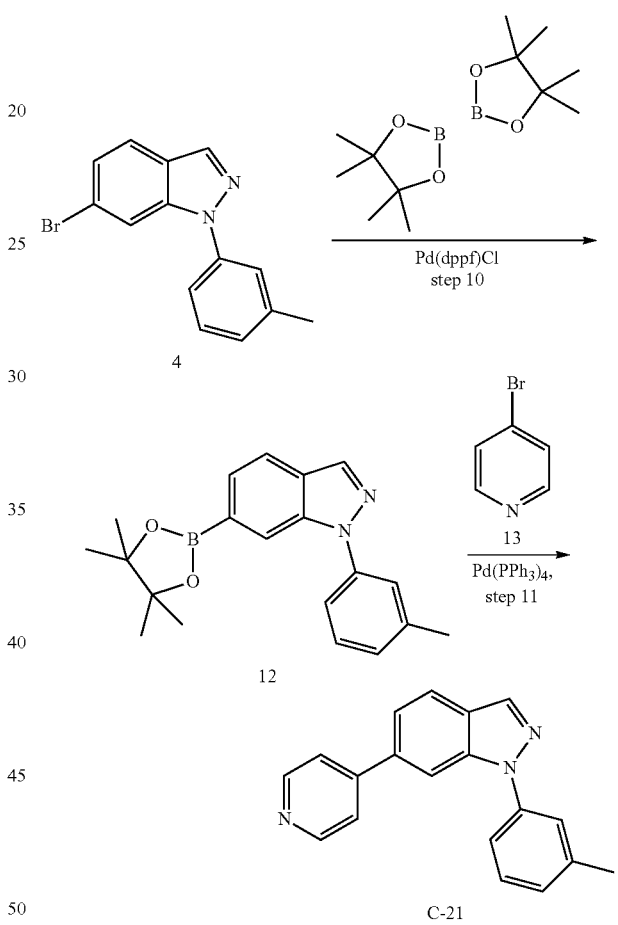

Referring to Reaction Scheme R12, at Step 10:

Compound 4 (0.1 g, 0.335 mmol, 1 eq.) was dissolved in 1,4-dioxane (5 mL) were added bis(pinnacaloto)-diboron (0.17 g, 0.671 mmol, 2 eqs.) followed by potassium acetate (0.098 g, 1.0 mmol, 3 eqs.). Degassing was done for 15 min, then [1, 1'-bis (diphenylphosphino)ferrocene] palladium(II) chloride with dichloromethane (0.027 g, 0.0335 mmol, 0.1 eq) was added under inert atmosphere. The reaction mixture was stirred and heated at 110° C. for 4 h, under nitrogen atmosphere. The progress of the reaction was monitored by tlc taking 4 as a limiting reactant. The reaction mixture was filtered through celite and was washed well with ethyl acetate. The filtrate was extracted with ethyl acetate (2×30 mL). The organic extracts were combined, washed with brine and dried using Na$_2$SO$_4$ then evaporated to obtain a viscous dark brown as a crude compound 12 (0.12 g). Compound 12 used for the Suzuki coupling reaction without purification. ESIMS: 334 (M+1)

Referring to Reaction Scheme R12, at Step 11:

To a solution of compound 12 (0.04 g, 0.119 mmol, 1 eq.) in dioxane (5 mL) was added compound 13 (0.038 gm, 0.239 mmol, 2 eqs.) followed by addition of 2M $K_2CO_3$ (0.041 gm, 0.297 mmol, 2.5 eqs.). Degassing was done for 15 min, and then Pd(PPh$_3$)$_4$ (0.007 g, 0.0059 mmol, 0.05 eqs.) was added under inert atmosphere. The reaction mixture was heated at 120° C. for 18 hrs. The progress of the reaction was monitored by t/c taking 9 as a limiting reactant. After completion of reaction, excess of solvent was evaporated under reduced pressure and reaction mass was extracted with DCM (2×30 mL) DCM, washed with brine and dried over anhydrous sodium sulphate and evaporated to get viscous dark brown material which was purified on silica gel chromatography with 40% EtOAC/Hexane to obtain compound C-21 as shown in Table 1 as pale yellow solid (0.008 g).

A variety of compounds including: C-22, C-23, and C-24, as shown in Table 1, may be synthesized following scheme R11 by using appropriate bromo reagents Example 5

This example demonstrates the synthesis of N-(1-(m-tolyl)-1H-indazol-6-yl)azetidine-3-carboxamide (compound C-25 as shown in Table 1).

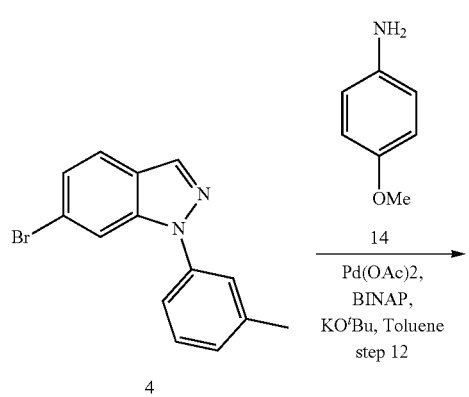

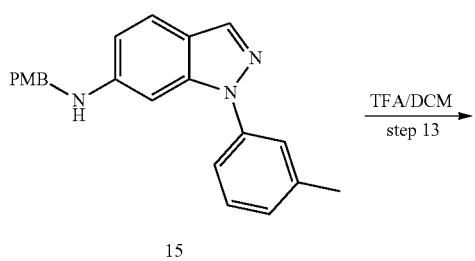

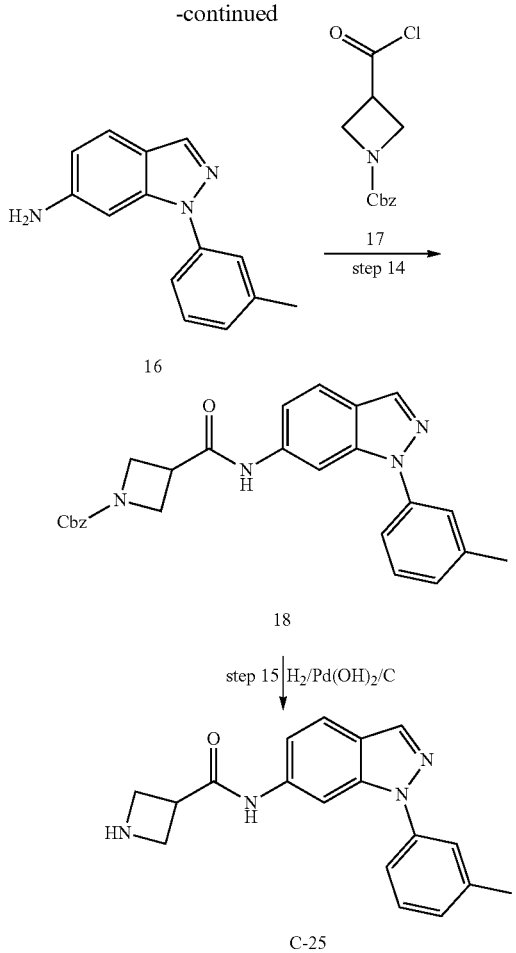

Referring to Reaction Scheme R13, at Step 12:

To a solution of compound 4 (0.9 g, 3.10 mmol, 1 eq.) in toluene (30 mL) was added successively compound 14 (0.56 g, 4.03 mmol, 1.3 eqs.) and KO$^t$Bu (1.4 g, 12.4 mmol, 4 eqs.). Degassing was done for 15 min, and then BINAP (0.385 g, 0.62 mmol, 0.2 eq) and Pd(OAc)$_2$ (0.070 g, 0.310 mmol, 0.1 eq) were added under inert atmosphere. The reaction mixture was heated at 120° C. for 4 hrs. The progress of the reaction was monitored by tlc taking 4 as a limiting reactant. After completion of reaction, reaction mixture was diluted with ethyl acetate (100 mL). Combined organic layers were washed with water (30 mL) followed by brine solution (30 mL). The organic layer thus obtained was dried over anhy Na$_2$SO$_4$ and concentrated to get crude product. The crude product was purified via column chromatography using 10% mixture of ethyl acetate in hexane as eluent to obtain 15 as pure compound (0.450 g).

Referring to Reaction Scheme R13, at Step 13:

To a solution of compound 15 (0.4 g, 1.21 mmol, 1 eq.) in ethanol (40 ml) was added successively 10% palladium hydroxide on carbon (0.040 g). The reaction mixture was stirred at room temperature under hydrogen atmosphere for 18 hrs. The progress of the reaction was monitored by tlc taking 15 as a limiting reactant. After completion of reaction, reaction mixture was filtered through celite and washed with 100 mL ethanol. Ethanol was dried under reduced pressure to obtain compound 16 (0.2 g).

Referring to Reaction Scheme R13, at Step 14:

To a solution of compound 16 (0.2 g, 0.89 mmol, 1 eq.) in DCM (20 mL) were added successively TEA (0.360 g, 3.57 mmol, 4 eqs.) followed by compound 17 (0.48 g, 1.78 mmol, 2 eqs) at 0° C. temperature. The reaction mixture was stirred at room temperature for 4 hrs. The progress of the reaction was monitored by tlc taking 16 as a limiting reactant. After completion of reaction, the excess of solvent was dried under reduced pressure. The crude reaction mixture was purified via column chromatography using 50% mixture of ethyl acetate in hexane as eluent to obtain 18 as pure compound (0.110 g).

Referring to Reaction Scheme R13, at Step 15:

To a solution of compound 18 (0.1 g, 0.23 mmol, 1 eq.) in ethanol (10 mL) was added successively 10% palladium hydroxide on carbon (0.020 g). The reaction mixture was stirred at room temperature under hydrogen atmosphere for 18 hrs. The progress of the reaction was monitored by tlc taking 18 as a limiting reactant. After completion of reaction, reaction mixture was filtered through celite and washed with 50 mL ethanol. Ethanol was dried under reduced pressure to obtain crude compound. Crude compound was purified via column chromatography using 2% mixture of methanol in DCM as eluent to obtain compound C-25 as shown in Table 1 as pure compound (0.070 g).

Example 6

This example demonstrates the synthesis of 1-phenyl-N-(piperidin-4-yl)-1H-indazole-6-carboxamide (compound C-26 as shown in Table 1).

R14

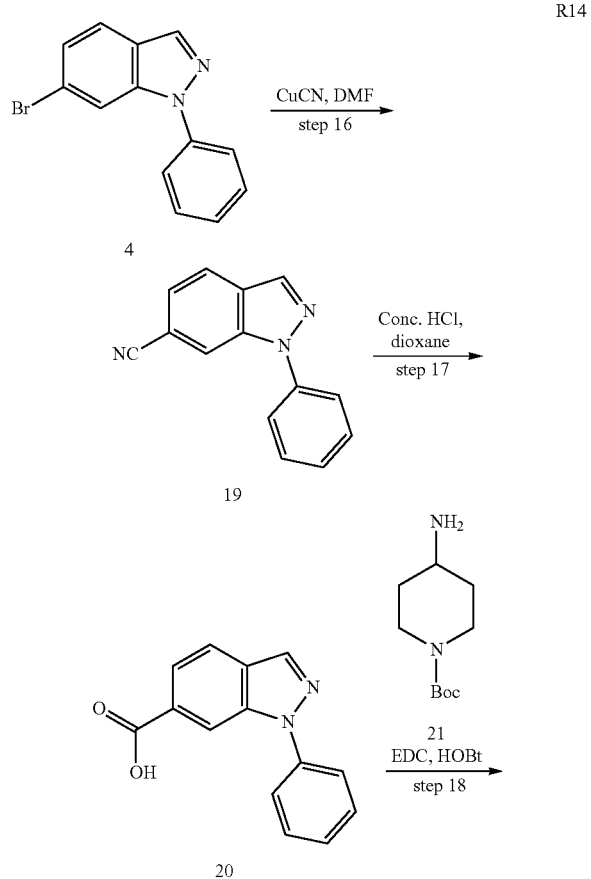

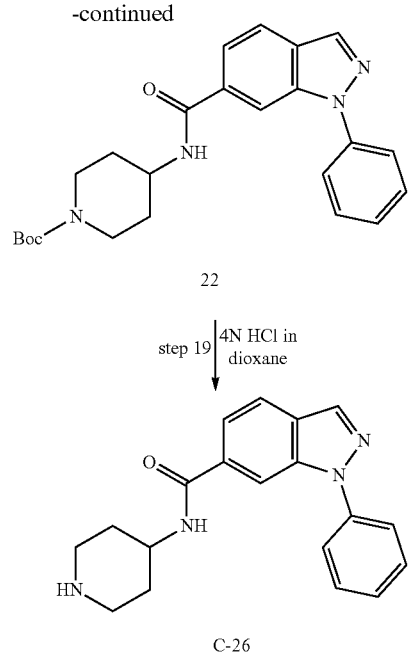

Referring to Reaction Scheme R14, at Step 16:

To a solution of compound 4 (2 g, 7.32 mmol, 1 eq.) in DMF (30 mL) was added successively copper cyanide (1.63 g, 18.3 mmol, 2.5 eqs.). The reaction mixture was heated at 150° C. for 24 hrs. The progress of the reaction was monitored by tlc taking 4 as a limiting reactant. After completion, it was poured into the ice and precipitated out. It was filtered under suction and dried to get the crude product. The crude reaction mixture was purified via column chromatography using 15% mixture of ethyl acetate in hexane as eluent to obtain 19 as pure compound (1.2 g).

Referring to Reaction Scheme R14, at Step 17:

Compound 19 (1.2 g, 5.4 mmol, 1 eq.) was taken in dioxane (2 mL) and Conc HCl (10 ml). The reaction mixture was heated at 130° C. for 18 hrs. The solvent was evaporated and crude was purified by column chromatography in solvent system 1% MeOH in DCM to get compound 20 (0.71 g).

Referring to Reaction Scheme R14, at Step 18:

To a solution of compound 20 (0.07 g, 0.294 mmol, 1 eq.) in DMF (3 mL) was added EDC.HCl (0.084 g, 0.441 mmol, 1.5 eq.) and HOBt (0.059 g, 0.441 mmol, 1.5 eq.) then stirred at RT for 20 mins. DIPEA (0.113 g, 0.882 mmol, 3 eqs.) and compound 10 (0.064 g, mmol, 0.323 mmol, 1.1 eqs.) were added in to the reaction mixture and stirred at RT for 18 hr. Reaction mass was diluted with DCM and washed with water and brine solution dried over anhydrous sodium sulphate, and then evaporated to obtain a viscous dark brown material. Purification of the solid residue was done by column chromatography in a solvent system of 1% MeOH in DCM to obtain compound 22 (0.075 g).

Referring to Reaction Scheme R14, at Step 19:

To a solution of compound 22 (0.050 g, 0.119 mmol, 1 eq.) in DCM (5 mL) was added dioxane HCl (4 M) 1 mL at 0° C. temperature. The reaction mixture was stirred at room temperature for 6 hrs. The progress of the reaction was monitored by tlc taking 22 as a limiting reactant. After completion of reaction, excess of solvent was evaporated under reduced pressure to obtain compound. Crude compound was purified by column chromatography using 4% mixture of methanol in DCM as eluent to get compound C-26 as shown in Table 1 (0.023 g).

Example 7

This example demonstrates the synthesis of 1-(6-(2-aminopyridin-4-yl)-1-(m-tolyl)-1H-indazol-3-yl)ethane-1,2-diol (compound C-27 as shown in Table 1).

limiting reactant. After completion of reaction, the excess of solvent was dried under reduced pressure. The crude reaction mixture was purified via column chromatography using 20-25% mixture of ethyl acetate in hexane as eluent to obtain 23 as pure compound (0.51 g).

Referring to Reaction Scheme R15, at Step 21:

To a solution of compound 23 (0.2 g, 0.619 mmol, 1 eq.) in dioxane (5 mL) of 2M solution of $K_2CO_3$ (0.256 g, 1.857

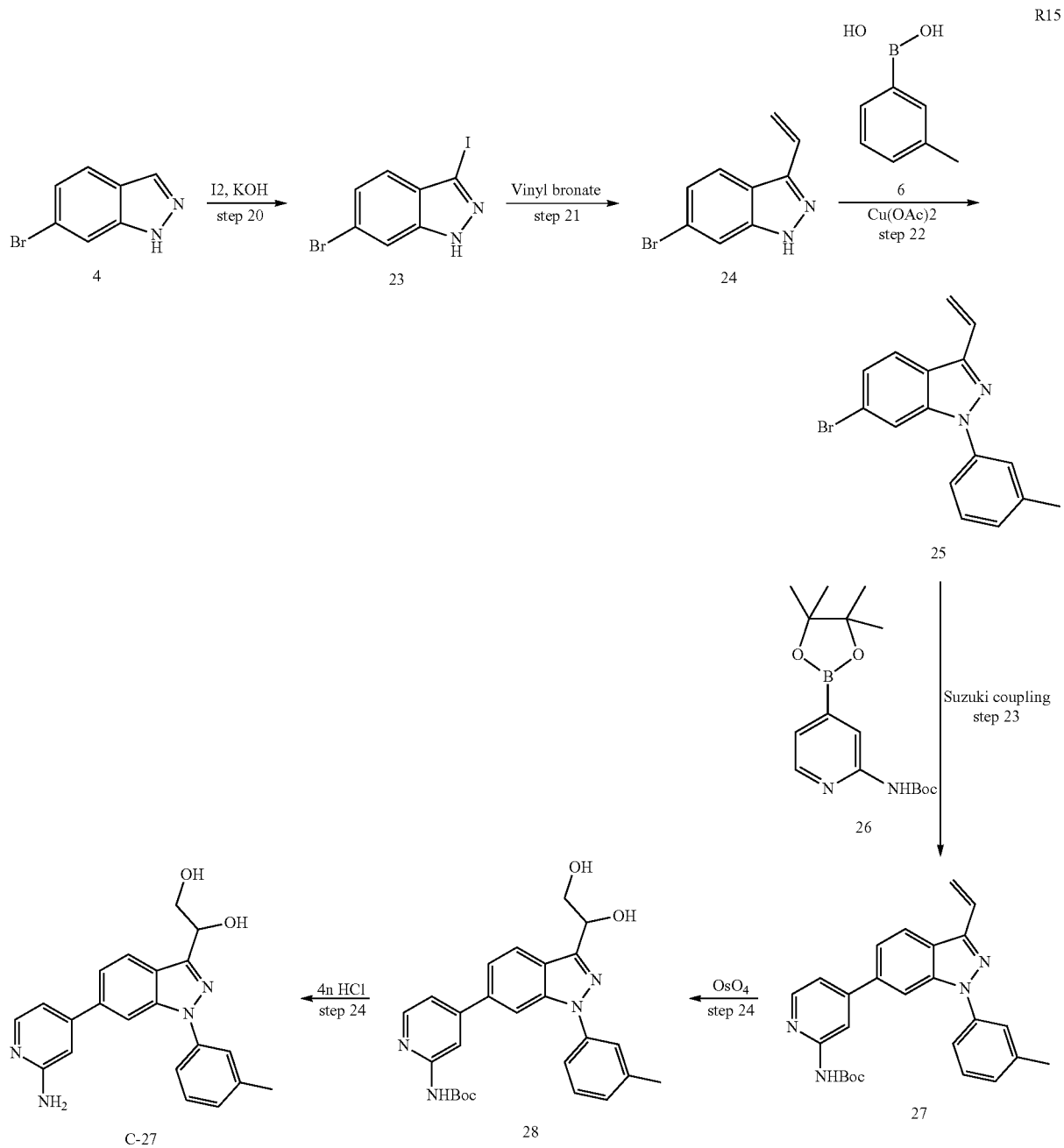

Referring to Reaction Scheme R15, at Step 20:

To a solution of compound 4 (0.5 g, 2.53 mmol, 1 eq.) in DMF (5 mL) was added KOH (0.284 g, 5.07 mmol, 2 eqs.). Now iodine (0.964 g, 3.79 mmol, 1.5 eqs.) the reaction mixture was stirred at room temperature for 4 hrs. The progress of the reaction was monitored by t/c taking 4 as a mmol, 3 eqs.) was added followed by addition of vinyl boronic acid (0.123 g, 0.789 mmol, 1.3 eqs.). After that $Pd(PPh_3)_4$ (0.035 g, 0.030 mmol, 0.05 eq) was added and reaction was heated under inert condition at 90° C. for 18 hrs. Dioxane was removed under vacuum and reaction mass was extracted with DCM (2×50 mL), washed with brine and dried over anhydrous sodium sulphate and evaporated to get viscous dark brown material which was purified on silica gel chromatography with 40% mixture of ethyl acetate in hexane as eluent to obtain compound 24 as pale yellow solid (0.087 g).

Referring to Reaction Scheme R15, at Step 22:

To a solution of compound 24 (0.2 g, 0.90 mmol, 1 eq.) and 3-methylphenyl boronic acid 6 (0.394 g, 1.79 mmol, 2.0 eqs.) in a DCM and triethylamine (0.181 g, 1.79 mmol, 2.0 eqs.) were added. The reaction mixture was stirred at 0° C. After 10 minutes, Cu(OAc)$_2$ (0.179 g, 0.9 mmol, 1.0 eq.) was added in the above reaction mixture and stirred for about 3 hours. The progress of the reaction was monitored by tlc taking 24 as a limiting reactant. After completion of reaction, reaction mixture was filtered by using filter paper and the filtrate was washed with ethyl acetate and water mixture. The organic layer was extracted and dried over anhy Na$_2$SO$_4$ and concentrated to get crude product. The crude product was purified via column chromatography using 5% mixture of ethyl acetate in hexane as eluent to obtain 25 as pure compound (0.115 g).

Referring to Reaction Scheme R15, at Step 23:

To a solution of compound 25 (0.115 gm, 0.366 mmol, 1 eq) in dioxane (5 mL) of 2M K$_2$CO$_3$ (0.150 g, 1.05 mmol, 3 eqs.) was added followed by addition of compound 26 (0.149 mg, 0.475 mmol, 1.3 eqs.). After that Pd(PPh$_3$)$_4$ (0.020 g, 0.017 mmol, 0.05 eq) was added and reaction was heated under inert condition at 110° C. for overnight. The progress of the reaction was monitored by tlc taking 25 as a limiting reactant. After completion of reaction, reaction mixture was filtered by using filter paper and the filtrate was washed with ethyl acetate and water mixture. The organic layer was extracted and dried over anhyd. Na$_2$SO$_4$ and concentrated to get crude product. The crude product was purified via column chromatography using 10% mixture of ethyl acetate in hexane as eluent to obtain 27 as pure compound (0.035 g).

Referring to Reaction Scheme R15, at Step 24:

To a solution of compound 27 (0.025 g, 0.058 mmol, 1 eq.) in tBuOH (5 mL) and acetone (5 mL) was added successively $^t$BuH$_2$O$_2$ (0.007 g, 0.087 mmol, 1.5 eqs.) and OsO4 (0.004 g, 0.002 mmol, 0.04 eq). The reaction mixture was stirred at room temperature for 24 hrs. The progress of the reaction was monitored by tlc taking 27 as a limiting reactant. After completion of reaction, the excess of solvent was dried under reduced pressure. The crude reaction mixture was purified via column chromatography using 20-25% mixture of ethyl acetate in hexane as eluent to obtain 28 as pure compound (0.010 g).

Referring to Reaction Scheme R15, at Step 25:

To a solution of compound 28 (0.010 mg, 0.0217 mmol, 1 eq.) in DCM (5 mL) was added dioxane HCl (4 M) 0.5 mL at 0° C. temperature. The reaction mixture was stirred at room temperature for 6 hrs. The progress of the reaction was monitored by tlc taking 28 as a limiting reactant. After completion of reaction, excess of solvent was evaporated under reduced pressure to obtain compound. Crude compound was purified by column chromatography using 2% mixture of methanol in DCM as eluent to get compound C-27 as shown in Table 1 (0.0025 g).

Example 8

This example demonstrates the synthesis of 4-(3-cyclopropyl-1-phenyl-1H-indazol-6-yl)pyridin-2-amine (compound C-28 as shown in Table 1).

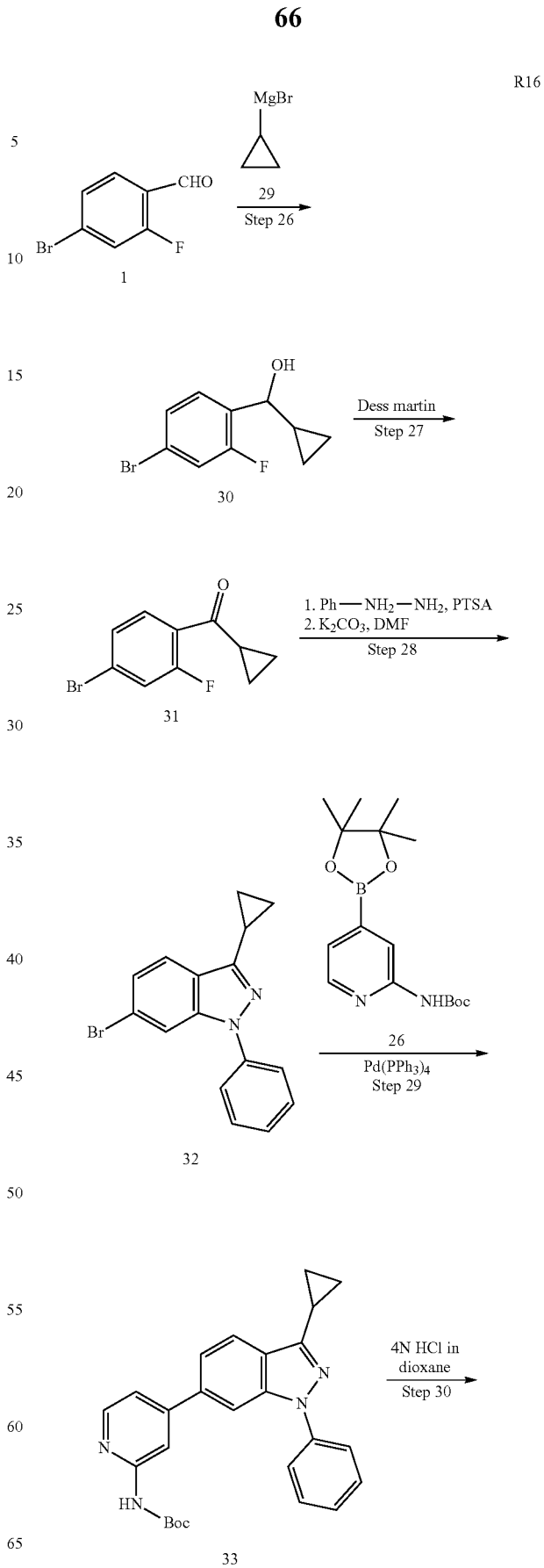

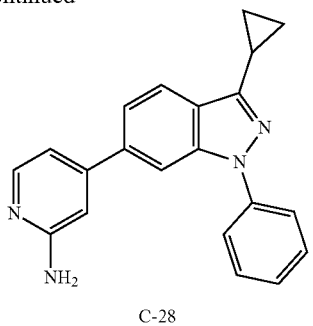

C-28

Referring to Reaction Scheme R16, at Step 26:

To a solution of compound 1 (2 g, 9.85 mmol, 1 eq.) in dry THF (15 ml) was added successively cyclopropyl magnesium bromide (1 N) 29 (19.7 g, 19.7 mmol, 2 eqs.) at −30° C. The reaction mixture was slowly brought to rt and stirred at room temperature for 3 hrs. The progress of the reaction was monitored by tlc taking 1 as a limiting reactant. After completion of reaction, 50 ml diethyl ether followed by 0.5 ml cold water were dropwise added into the reaction mass at 0° C. temperature. Reaction mixture was filtered and filtrate was concentrated to get crude product. The crude reaction mixture was purified via column chromatography using 15% mixture of ethyl acetate in hexane as eluent to obtain 30 as pure compound (Yield: 1.1 g).

Referring to Reaction Scheme R16, at Step 27:

To a solution of compound 30 (0.7 g, 2.85 mmol, 1 eq.) in DCM (75 ml) was added successively Dess Martin (1.81 g, 4.28 mmol, 1.5 eqs.). The reaction mixture was stirred at 00° C. for 4-5 hrs. The progress of the reaction was monitored by tlc taking 30 as a limiting reactant. After completion of reaction, reaction mixture was washed with ethyl acetate and water. The organic layer was extracted and dried over anhy $Na_2SO_4$ and concentrated to get crude product. The crude product was purified via column chromatography using 5% mixture of ethyl acetate in hexane as eluent to obtain 31 as pure compound. (Yield: 0.49 g)

Referring to Reaction Scheme R16, at Step 28:

To a solution of compound 31 (0.49 g, 2.01 mmol, 1 eq.) and phenyl hydrazine (0.239 g, 2.21 mmol 1.1 eqs.) in ethanol (50 mL) was added successively PTSA (0.030 g). The reaction mixture was stirred at 70° C. for 3 hrs. The progress of the reaction was monitored by tlc taking 31 as a limiting reactant. After completion of reaction, the excess of solvent was dried under reduced pressure. $K_2CO_3$ (1.1 g, 8.04 mmol, 4 eqs.) was added in the above reaction mixture in DMF (10 mL). The reaction mixture was stirred at 140° C. for overnight. The progress of the reaction was monitored by tlc. After completion, it was poured into the ice and precipitated out. It was filtered under suction and dried to get the crude product. The crude reaction mixture was purified via column chromatography using 5% mixture of ethyl acetate in hexane as eluent to obtain 32 as pure compound (0.3 g).

Referring to Reaction Scheme R16, at Step 29:

To a solution of compound 32 (0.1 gm, 0.319 mmol, 1 eq) in dioxane (5 mL) 2M solution of $K_2CO_3$ (0.132 gm, 0.956 mmol, 3 eqs.) was added followed by addition of compound 26 (0.205 mg, 0.638 mmol, 2 eqs.). After that $Pd(PPh_3)_4$ (0.018 g, 0.015 mmol, 0.05 eq) was added and reaction was heated under inert conditions at 100° C. for 4 hrs. The progress of the reaction was monitored by tlc taking 32 as a limiting reactant. After completion of reaction, reaction mixture was filtered by using filter paper and the filtrate was washed with ethyl acetate and water mixture. The organic layer was extracted and dried over anhydrous $Na_2SO_4$ and concentrated to get crude product. The crude product was purified via column chromatography using 5% mixture of ethyl acetate in hexane as eluent to obtain 33 as pure compound (70 mg).

Referring to Reaction Scheme R16, at Step 30:

To a solution of compound 33 (0.06 g, 0.140 mmol, 1 eq.) in DCM (5 mL) was added dioxane HCl (4 M) 0.5 mL at 0° C. temperature. The reaction mixture was stirred at room temperature for 6 hrs. The progress of the reaction was monitored by tlc taking 28 as a limiting reactant. After completion of reaction, excess of solvent was evaporated under reduced pressure to obtain compound. Crude compound was purified by column chromatography using 2% mixture of methanol in DCM as eluent to get compound C-28 as shown in Table 1 (0.030 g).

Example 9

This example demonstrates the synthesis of 6-(piperidin-4-yl)-1-(m-tolyl)-1H-indazole (compound C-29 as shown in Table 1).

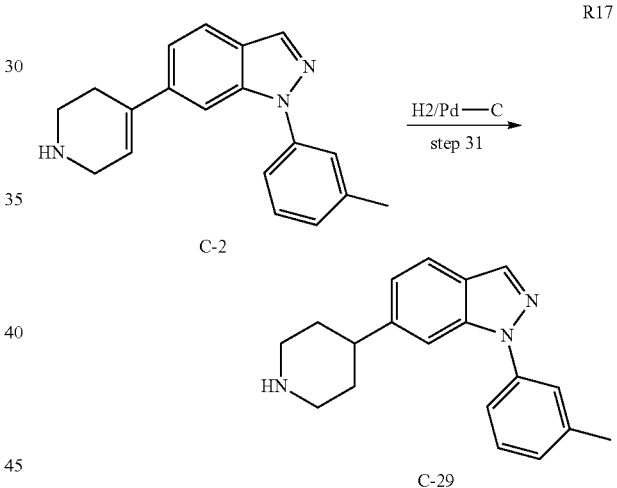

Referring to Reaction Scheme R17, at Step 31:

To a solution of compound C-2 as shown in Table 1 (25 mg, 0.086 mmol, 1 eq.) in ethanol (5 ml) was added successively 10% palladium on carbon (10 mg). The reaction mixture was stirred at room temperature under hydrogen atmosphere for 18 hrs. The progress of the reaction was monitored by tlc taking compound C-2 as shown in Table 1 as a limiting reactant. After completion of reaction, reaction mixture was filtered through celite and washed with 50 mL ethanol. Ethanol was dried under reduced pressure to obtain crude compound. Crude compound was purified via column chromatography using 2% mixture of methanol in DCM as eluent to obtain compound C-29 as shown in Table 1 as pure compound (0.014 g).

Example 10

This example demonstrates the synthesis of 1-benzyl-6-(1,2,3,6-tetrahydropyridin-4-yl)-1H-indazole (compound C-30 as shown in Table 1).

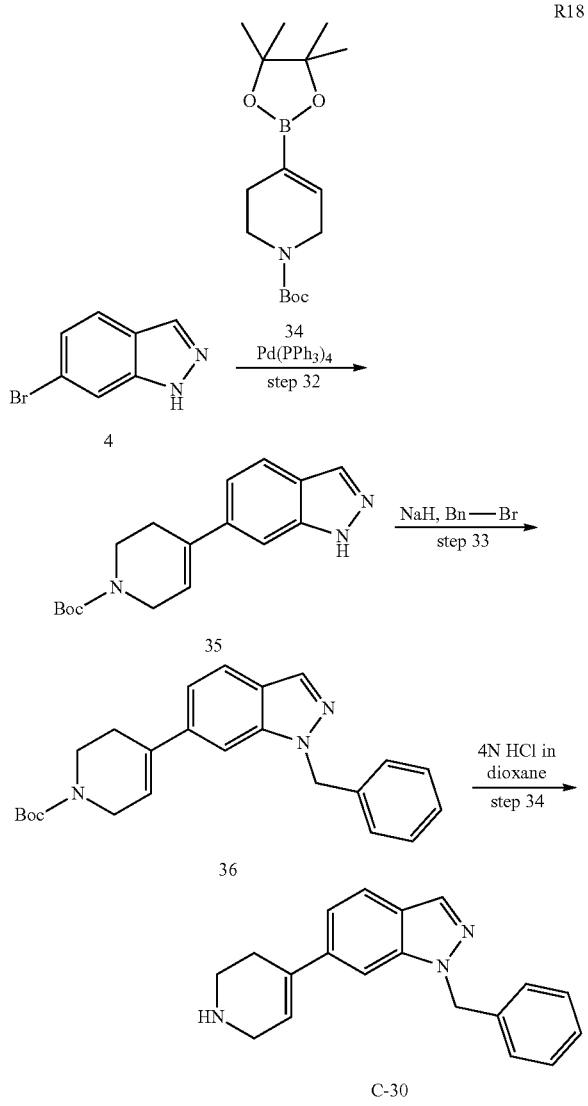

Referring to Reaction Scheme R18, at Step 32:

To a solution of compound 4 (2 g, 10.1 mmol, 1 eq) in dioxane (80 mL) was added successively compound 34 (4.08 g, 7.8 mmol, 1.3 eq.) and 2 (M) solution of $K_2CO_3$ (5.12 g, 26 mmol, 3 eq). Degassing was done for 15 min, and then $Pd(PPh_3)_4$ (0.3 g, 0.26 mmol, 0.05 eq) was added under inert atmosphere. The reaction mixture was heated at 120° C. for 6 hrs. Excess of solvent was removed under vacuum and the reaction mass was diluted with water and extracted with ethyl acetate (3×50 ml). Combined organic layers were washed with water (50 ml) followed by brine solution (50 ml). The organic layer thus obtained was dried over anhy $Na_2SO_4$ and concentrated to get crude product. The crude product was purified via column chromatography using 25% mixture of ethyl acetate in hexane as eluent to obtain 35 as pure compound (1.2 g).

Referring to Reaction Scheme R18, at Step 33:

To a solution of compound 35 (0.12 mg, 0.401 mmol, 1 eq.) in DMF (3 ml) was added successively NaH (50%) (0.028 g, 0.602 mmol, 1.5 eqs.) at 00° C. temperature. The reaction mixture was stirred at 0° C. temperature for 30 mins. Now Benzyl bromide (0.075 g, 0.441 mmol, 1.1 eqs.) was drop wise added into the reaction mass and reaction mixture was stirred at room temperature under hydrogen atmosphere for 6 hrs. The progress of the reaction was monitored by tlc taking 35 as a limiting reactant. Reaction mixture was poured into the ice and solid precipitated out. Solid was filtered under suction and dried to get the crude product. Crude compound was purified via column chromatography using 1% mixture of methanol in DCM as eluent to obtain 36 as pure compound (75 mg).

Referring to Reaction Scheme R18, at Step 34:

To a solution of compound 8 (75 mg, 0.192 mmol, 1 eq) in DCM (10 mL) was added dioxane HCl (4 M) 1 ml at 00° C. temperature. The reaction mixture was stirred at room temperature for 6 hrs. The progress of the reaction was monitored by tlc taking 8 as a limiting reactant. After completion of reaction, excess of solvent was evaporated under reduced pressure to obtain compound 3. Crude compound was purified by column chromatography using 4% mixture of methanol in DCM as eluent to get compound C-5 as shown in Table 1 (12 mg).

Example 11

Screening for KHK Inhibition.

Specific high-throughput screening assays were developed for KHK-C and KHK-A using recombinant proteins. Purified human recombinant KHK-C and KHK-A were produced using the Bio-Rad Profinity eXact Fusion-Tag System and Profinia protein purification instrument. The assays consist of a 3-step, coupled-enzyme process involving fructokinase (KHK), pyruvate kinase (PK) and lactate dehydrogenase (LDH).[1,2] The disappearance of NADH is measured kinetically by $A_{340}$ at 37° C. The enzymatic assay was carried out in a total reaction volume of 200 ul containing 50 mM PIPES, 6 mM $MgCl_2$, 100 mM KCl, 100 uM-5 mM ATP, 2 mM phosphoenolpyruvate, 0.3 mM NADH, 15 U of pyruvate kinase, 15 U of lactate dehydrogenase, and 75-1000 ng KHKC. 1 mM fructose was added to the reactions, except for the no fructose controls which utilized water. The high-throughput assay was used to identify inhibitors that have an $IC_{50}$ value <5 μM for KHK-C.[5] The '559 pub also sets forth a KHK assay for testing inhibition activity of potential KHK inhibitors.

Table 2 shows select exemplary therapeutic agents of according to various embodiments and their $IC_{50}$ as determined using the 3-step KHK assay described in Example 11.

TABLE 2

| Compound | Structure | $IC_{50}$ Result |
|---|---|---|
| C-5 | 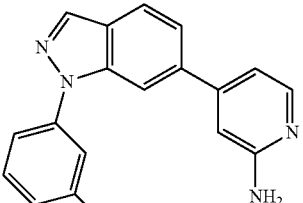 | 280 nM |
| C-1 | 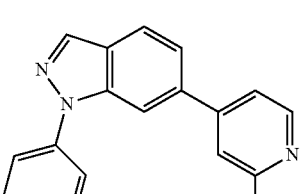 | 1.170 nM |

TABLE 2-continued

| Compound | Structure | IC$_{50}$ Result |
|---|---|---|
| C-28 | 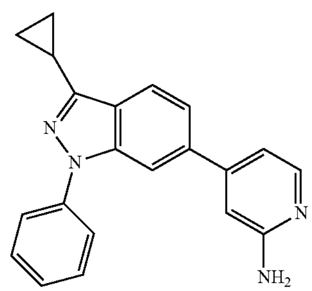 [SMILES: Nc1cc(-c2ccc3c(C4CC4)nn(-c4ccccc4)c3c2)ccn1] | 700 nM |
| C-33 | 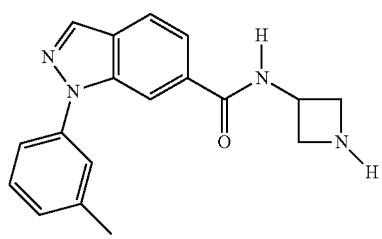 [SMILES: Cc1cccc(-n2ncc3ccc(C(=O)NC4CNC4)cc32)c1] | 2,300 nM |
| C-34 | 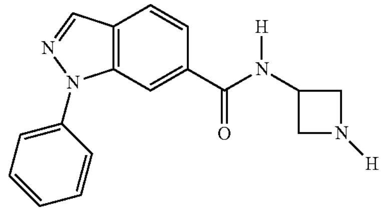 [SMILES: O=C(NC1CNC1)c1ccc2cnn(-c3ccccc3)c2c1] | 580 nM |
| C-40 | 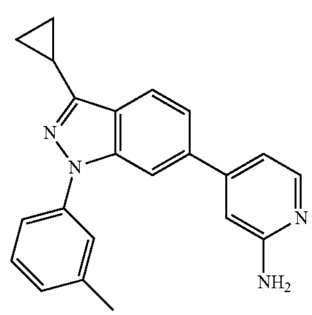 [SMILES: Cc1cccc(-n2nc(C3CC3)c3ccc(-c4ccnc(N)c4)cc32)c1] | |
| C-32 | 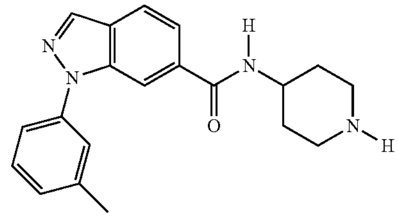 [SMILES: Cc1cccc(-n2ncc3ccc(C(=O)NC4CCNCC4)cc32)c1] | 790 nM |
| C-26 | 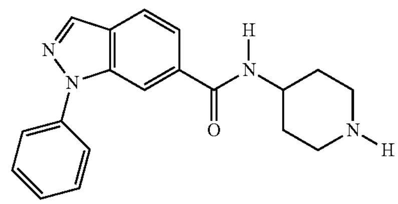 [SMILES: O=C(NC1CCNCC1)c1ccc2cnn(-c3ccccc3)c2c1] | 2,300 nM |
| C-25 | | 510 nM |
| C-72 | | 1200 nM |

Examples 12

Example 12 describes fructokinase inhibition results and fructose-induce hypoglycemia prevention results obtained from in vivo assay in in Aldolase B Knockout Mice. Hereditary Fructose intolerance is a rare genetic disease due to deficiency of aldolase B that is associated with over activation of KHK-C. One of the key features in these individuals is the development of acute hypoglycemia following exposure to fructose ingestion due to rapid uptake of glucose into the liver with the formation of glycogen. Recently, an aldolase-B KO (aldoB$^{-/-}$) mouse that has the clinical features of HFI in humans was developed. These mice develop immediate dose-dependent hypoglycemia in response to fructose, but also develop fatty liver within days of low grade fructose feeding. It was observed that the development of hypoglycemia in the aldoB$^{-/-}$ mouse was completely prevented in mice lacking both aldoB and fructokinase, thereby documenting that the hypoglycemic response is mediated by fructokinase. In addition, injection of fructose into the aldoB$^{-/-}$ KO mouse injected with inhibitors according to various embodiments are also protected from the development of hypoglycemia.

The procedure used in Example 12 consisted of first fasting animals for six hours, followed by the administration of fructose by oral gavage (45 mg fructose, equivalent to 1.5 g/kg body weight) or vehicle (water) to mice and following serum glucose levels over 90 minutes by measuring glucose with a glucometer from tail snip bleeds. With vehicle administration serum glucose stays normal, but when fructose is administered to aldolase B knockout mice a progressive fall in serum glucose occurs, as noted by the percent (%) of the baseline level.

Example 12 shows the effect of intraperitoneally administered C-25 (as shown in Table 1 and below) to prevent the hypoglycemic response to fructose.

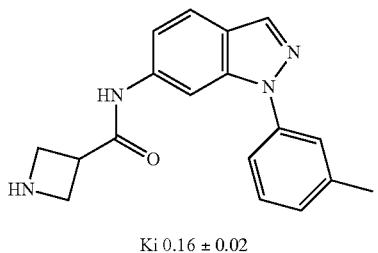

C-25

Ki 0.16 ± 0.02

Specifically, mice in Group 1 then were given C-25 by intraperitoneal (IP) route (25 mg/kg IP 30 min before with a repeated dose at the time of the oral fructose gavage), the hypoglycemic response was prevented and the glucose levels remained similar to vehicle administered mice. In contrast, when fructose was given by gavage without drug the hypoglycemic response developed, similar to what we have reported with fructose alone. These studies show that the IP injection of C-25 may be used to prevent fructose-induced hypoglycemia in the aldoB$^{-/-}$ KO mice, which we know is mediated by fructokinase. The results of Example 12 are summarized in FIG. 1.

REFERENCES

The teachings of the following references, which are not admitted to be prior art by inclusion in this section, are incorporated herein by reference in their entirety to the extent that they are not inconsistent with the teachings herein.

1. Van den Berghe G, Bronfman M, Vanneste R, Hers H G. The mechanism of adenosine triphosphate depletion in the liver after a load of fructose. A kinetic study of liver adenylate deaminase. *Biochem J.* 1977; 162(3):601-609.
2. Ishimoto, T., M. A. Lanaspa, M. T. Le, et al. 2012. Opposing effects of fructokinase C and A isoforms on fructose-induced metabolic syndrome in mice. Proc Natl Acad Sci USA. 109: 4320-4325.
3. Li, X., X. Qian, L. X. Peng, et al. 2016. A splicing switch from ketohexokinase-C to ketohexokinase-A drives hepatocellular carcinoma formation. Nat Cell Biol. 18: 561-571.
4. Lanaspa, M. A., T. Ishimoto, N. Li, et al. 2013. Endogenous fructose production and metabolism in the liver contributes to the development of metabolic syndrome. Nat Commun. 4: 2434.
5. Lanaspa, M. A., T. Ishimoto, C. Cicerchi, et al. 2014. Endogenous fructose production and fructokinase activation mediate renal injury in diabetic nephropathy. J Am Soc Nephrol. 25: 2526-2538.
6. Lanaspa M A. Kuwabara M, Andres-Hernando A, Li N, Cicerchi C, Jensen J, Orlicky D J, Roncal-Jimenez C, Ishimoto T, Nakagawa T, Rodriguez-lturbe B, MacLean P S, Johnson R J. High Salt Intake Causes Leptin Resistance and Obesity in Mice by Stimulating Endogenous Fructose Production and Metabolism Proc Natl Acad Sci USA PNAS Mar. 5, 2018. 201713837
7. Lanaspa M A, Andres-Hernando A, Orlicky D J, Cicerchi C, Jang C, Li N, Milagres T, Kuwabara M, Wempe M F, Rabinowitz J D, Johnson R J, Tolan D R. Ketohexokinase C blockade ameliorates fructose-induced metabolic dysfunction in fructose-sensitive mice. J Clin Invest (in press)
8. Andres-Hernando A, Li N, Cicerchi C, Inaba S, Chen W, Roncal-Jimenez C, Le M T, Wempe M F, Milagres T, Ishimoto T, Fini M, Nakagawa T, Johnson R J, Lanaspa M A. Protective role of fructokinase blockade in the pathogenesis of acute kidney injury in mice Nat Commun. 2017 Feb. 13; 8:14181
9. Roncal Jimenez, C. A., T. Ishimoto, M. A. Lanaspa, et al. 2014. Fructokinase activity mediates dehydration-induced renal injury. Kidney Int. 86: 294-302.
10. Mirtschink P, Krishnan J, Grimm F, et al. 2015. HIF-driven SF3B1 induces KHK-C to enforce fructolysis and heart disease. Nature. 522: 444-449.
11. Admyre T, Amrot-Fors L, Andersson M, Bauer M, Biursell M, Drmota T, Hallen S, Hartleib-Geschwindner J, Lindmark B, Liu J, LöfCren L, Rohman M, Selmi N, Wallenius K. Inhibition of AMP deaminase activity does not improve glucose control in rodent models of insulin resistance or diabetes Chem Biol 2014 Nov. 20; 21(11): 1486-96. doi: 10.1016/j.chembiol.2014.09.011.
12. Oppelt S A, Sennott E M, Tolan D R. Aldolase-B knockout in mice phenocopies hereditary fructose intolerance in humans. Mol Genet Metab. 2015; 114(3):445-450.
13. U.S. Pat. No. 6,894,047,
14. U.S. Pat. No. 6,570,013,
15. U.S. Pat. No. 6,294,538,
16. U S Published Patent Application No. 20050020578
17. U S Patent Pub. 20110263559
18. Adelman R C, Ballard F J, Weinhouse S. Purification and properties of rat liver fructokinase. J Biol Chem. 1967; 242(14):3360-3365.
19. Asipu A, Hayward B E, O'Reilly J, Bonthron D T. Properties of normal and mutant recombinant human ketohexokinases and implications for the pathogenesis of essential fructosuria. Diabetes. 2003; 52(9):2426-2432.
20. Zhang J H, Chung T D, Oldenburg K R. A Simple Statistical Parameter for Use in Evaluation and Validation of High Throughput Screening Assays. J Biomol Screen. 1999; 4(2):67-73.
21. Bais R, James H M, Rofe A M, Conyers R A. The purification and properties of human liver ketohexokinase. A role for ketohexokinase and fructose-bisphosphate aldolase in the metabolic production of oxalate from xylitol. Biochem J. 1985; 230(1):53-60.
22. Le M T, Lanaspa M A, Cicerchi C M, et al: Bioactivity-Guided Identification of Botanical Inhibitors of Ketohexokinase. PLoS One 11:e0157458, 2016.
23. Thurston J H, Jones E M, Hauhart R E. Decrease and inhibition of liver glycogen phosphorylase after fructose. An experimental model for the study of hereditary fructose intolerance. Diabetes. 1974; 23(7):597-604.
24. Van den Berghe G, Hue L, Hers H G. Effect of the administration of fructose on the glycogenolytic action of glycogen. Biochem J. 1973; 134:637.
25. Roncal Jimenez, C. A., T. Ishimoto, M. A. Lanaspa, et al. 2014. Fructokinase activity mediates dehydration-induced renal injury. Kidney Int. 86: 294-302.
26. Zhang, X., F. Song, G. H. Kuo, et al. 2011. Optimization of a pyrazole hit from FBDD into a novel series of indazoles as ketohexokinase inhibitors. Bioorg Med Chem Lett. 21: 4762-4767.
27. "Design of Prodrugs", ed. H. Bundgaard, Elsevier, 1985.
28. *Handbook of Pharmaceutical Excipients*, published by the American Pharmaceutical Association and the Pharmaceutical Society of Great Britain.
29. Methods of formulating pharmaceutical compositions have been described in numerous publications such as

What is claimed is:

1. A compound according to Formula I:

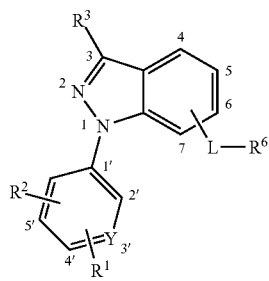

wherein R¹ and R² are independently selected from: —H, —C₁-C₅-alkyl, —C₃-C₅-cycloalkyl, —(CH₂)ₙ-C₃-C₅-cycloalkyl, —Cl, —Br, —CF₃, —CHF₂, —OCF₃, —OCHF₂, —O—C₃-C₅-cycloalkyl, —CN, —SO₂—C₁-C₄-alkyl, —SO₂CF₃, —SO₂—C₁-C₄-cycloalkyl, —Si(CH₃)₃, —C≡C—C₁-C₄-alkyl, and —C≡C—C₃-C₅-cycloalkyl;

wherein R³ is selected from: —H, -cyclopropyl, -cyclobutyl, —CH₂OCH₃, 3-oxetanyl, —O—C₃-C₅-cycloalkyl, —CH₂O—C₁-C₄-alkyl, and —CH₂O-C₃-C₅-cycloalkyl;

wherein R⁶ is selected from: —(CH₂)ₙ—N(R⁵)₂, 2-pyridyl, 3-pyridyl, 4-pyridyl, 3-pyridazinyl, 4-pyridazinyl, 1-piperazinyl, pyrimidin-2-yl, pyrimidin-4-yl, pyrimidin-5-yl, 4-piperidinyl, 3-piperidinyl, 3-azetidinyl, 3-pyrolidinyl, 3-imidazolyl, 4-imidazolyl, 1,2,4-oxadiazol-5-yl, 1,2,4-triazol-3-yl, benzimidazol-5-yl, and indol-5-yl, wherein each R₆ is optionally substituted with from 1 to 3 substituents selected from C₁-C₅-alkyl, C₁-C₅-cycloalkyl, —N(R⁵)₂, —Cl, —F, —Br, —OR⁵, —O—C₃-C₇-cycloalkyl, —CN, —CF₃, —CHF₂, —OCF₃, —OCHF₂, wherein L is selected from a covalent bond, —O—, —CONR⁵—, O—CH(R⁵)—, —CH₂OCH₂—, —CH(R⁵)—O—, —O(CH₂)₂—, —CO—, —(CH₂)ₙ—, and —CH(OH)—;

with the proviso that when L is selected from —CO, —O(CH₂)₂-, and —(CH₂)ₙ, R⁶ is selected from 2-azaspiro[3.3]heptan-6-yl, octahydropyrrolo[3,4-c]pyrrol-1-yl, 1-piperazinyl, 2,6-diazaspiro[3.3]heptan-1-yl,

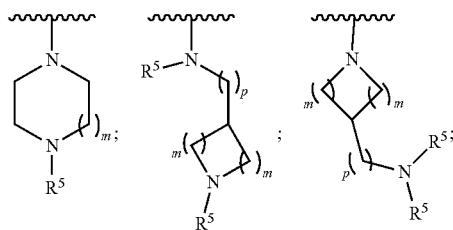

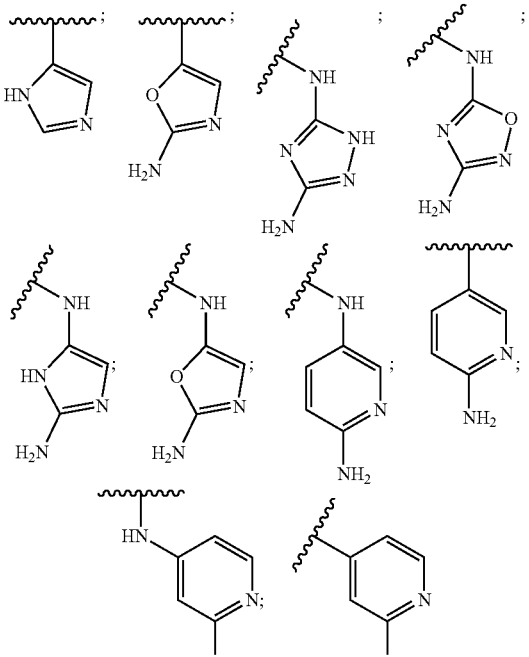

m = 1,2
p = 0, 1, 2, 3 wherein R⁵ is selected from —H, and C₁-C₅-alkyl;
wherein n is selected from 1, 2, 3, and 4;
wherein m is selected from 1 and 2,
wherein p is selected from 0, 1, 2, and 3; and
wherein Y is selected from N and CH.

2. The compound according to claim 1, wherein the compound is N-(1-(m-tolyl)-1H-indazol-6-yl)azetidine-3-carboxamide.

3. The compound according to claim 1, wherein administering the compound reduces a hypoglycemic response to fructose.

4. The compound according to claim 1, wherein the compound reduces a hypoglycemic response to fructose by an amount of at least 10, 20, 30, 40 or 50%.

5. A pharmaceutically acceptable salt of the compound according to claim 1.

6. A pharmaceutical composition comprising the compound according to claim 1 and a pharmaceutically acceptable carrier.

7. The pharmaceutical composition according to claim 6, further comprising at least one therapeutic conjunctive compound.

8. The pharmaceutical composition according to claim 7, wherein the at least one therapeutic conjunctive compound is at least one selected from: an angiotensin-converting enzyme (ACE) inhibitor, an aldosterone antagonist, an amphetamine, an amphetamine-like agent, an Angiotensin II receptor antagonist, an anti-oxidant, an aldose reductase inhibitor, a biguanide, a sorbitol dehydrogenase inhibitor, a thiazolidinedione, a glitazone, a thiazide diuretic, a thiazide-like diuretic, a triglyceride synthesis inhibitor, and an uric acid lowering agent.

9. A pharmaceutical composition produced by a process comprising mixing a compound according to claim 1 and a pharmaceutically acceptable carrier.

10. A process for making a pharmaceutical composition, the process comprising mixing a compound according to claim 1 and a pharmaceutically acceptable carrier.

11. A method of treating a disorder or disease mediated by ketohexokinase, the method comprising administering a therapeutically effective amount of the compound according to claim 1.

12. The method according to claim 11, wherein the disorder or disease mediated by ketohexokinase is selected from: obesity, elevated glucose levels, glucose intolerance, insulin resistance, Type I diabetes mellitus, Type II diabetes mellitus, Metabolic Syndrome X, elevated triglycerides, hyperlipidemia, and hypertension.

13. The method according to claim 12, wherein the disorder or disease mediated by ketohexokinase is selected from: obesity, Type II diabetes mellitus, and Metabolic Syndrome X.

\* \* \* \* \*